US012616516B2

(12) United States Patent
Takahashi

(10) Patent No.: US 12,616,516 B2
(45) Date of Patent: May 5, 2026

(54) MEDICAL DEVICE

(71) Applicant: TERUMO KABUSHIKI KAISHA, Tokyo (JP)

(72) Inventor: Yusuke Takahashi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 492 days.

(21) Appl. No.: 18/174,134

(22) Filed: Feb. 24, 2023

(65) Prior Publication Data

US 2023/0218341 A1 Jul. 13, 2023

Related U.S. Application Data

(63) Continuation of application No. PCT/JP2021/031128, filed on Aug. 25, 2021.

(30) Foreign Application Priority Data

Aug. 26, 2020 (JP) ................................. 2020-142445

(51) Int. Cl.
    *A61B 17/00* (2006.01)
    *A61B 18/00* (2006.01)
    *A61B 18/14* (2006.01)

(52) U.S. Cl.
    CPC ..................... *A61B 18/1492* (2013.01); *A61B 2017/00247* (2013.01); *A61B 2018/0016* (2013.01);
    (Continued)

(58) Field of Classification Search
    None
    See application file for complete search history.

(56) References Cited

U.S. PATENT DOCUMENTS

| | | | |
|---|---|---|---|
| 2013/0102869 A1* | 4/2013 | Kordis | ................. A61B 5/6859 |
| | | | 600/375 |
| 2014/0114304 A1 | 4/2014 | Wang et al. | |

(Continued)

FOREIGN PATENT DOCUMENTS

| | | | |
|---|---|---|---|
| WO | 2019085841 A1 | 5/2019 | |
| WO | WO-2019179447 A1 * | 9/2019 | ............. A61B 18/12 |

(Continued)

OTHER PUBLICATIONS

Translated WO 2019/179447 (Year: 2025).*

(Continued)

*Primary Examiner* — Linda C Dvorak
*Assistant Examiner* — Nicholas S Borsch
(74) *Attorney, Agent, or Firm* — BUCHANAN INGERSOLL & ROONEY PC

(57) ABSTRACT

A medical device includes an expansion body, an elongated shaft portion, and a plurality of electrode assemblies. The expansion body includes a recessed portion that is recessed radially inward. The recessed portion includes a radially innermost bottom portion including a proximal side curved portion and a distal side curved portion, a proximal side upright portion, and a distal side upright portion. Each of the plurality of electrode assemblies includes an electrode portion disposed along the expansion body from the proximal side upright portion or the distal side upright portion to the bottom portion so as to face a receiving space defined by the recessed portion. The proximal side curved portion and the distal side curved portion deform in response to expansion and contraction of the expansion body. The electrode portion is in a floating state with respect to the distal side curved portion and the proximal side curved portion.

22 Claims, 11 Drawing Sheets

(52) U.S. Cl.
CPC ............... *A61B 2018/00267* (2013.01); *A61B*
*2018/00357* (2013.01); *A61B 2018/00601*
(2013.01); *A61B 2018/142* (2013.01)

(56) References Cited

U.S. PATENT DOCUMENTS

| | | | |
|---|---|---|---|
| 2020/0069364 A1 | 3/2020 | Salahieh et al. | |
| 2020/0238059 A1* | 7/2020 | Wang ........................ | A61F 2/90 |
| 2022/0110679 A1* | 4/2022 | Wang ................. | A61B 18/1492 |

FOREIGN PATENT DOCUMENTS

| | | | |
|---|---|---|---|
| WO | 2019188916 A1 | 10/2019 | |
| WO | 2019189079 A1 | 10/2019 | |

OTHER PUBLICATIONS

International Search Report (PCT/ISA/210) with English translation and Written Opinion (PCT/ISA/237) mailed on Oct. 19, 2021, by the Japanese Patent Office as the International Searching Authority for International Application No. PCT/JP2021/031128.
Extended European Search Report dated Jan. 31, 2024, issued in corresponding European Application No. 21861603.5. (9 pages).

\* cited by examiner

FIG. 11
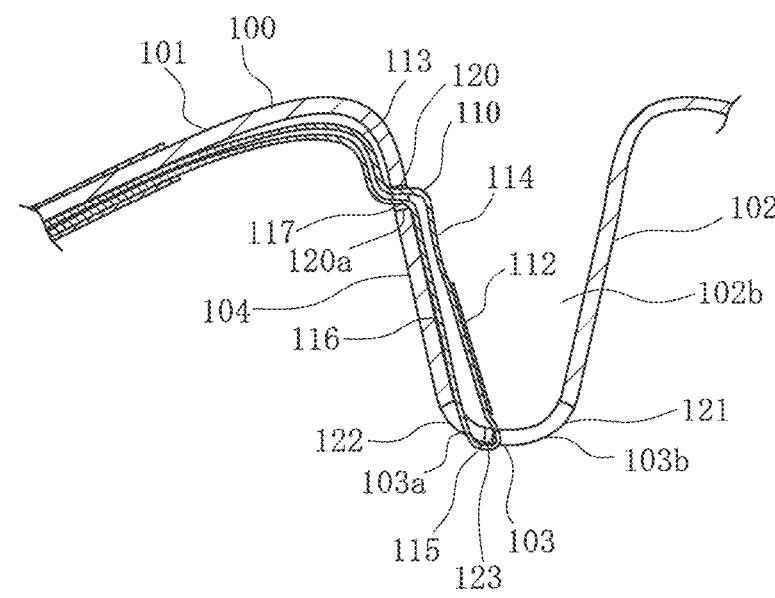
FIG. 12A
FIG. 12B
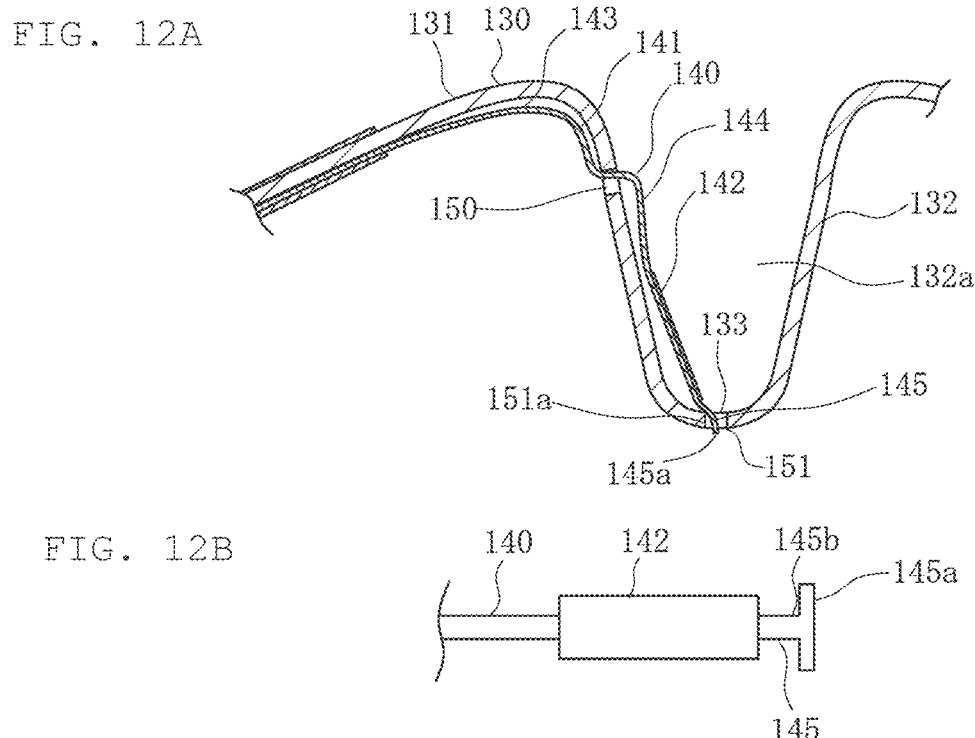

MEDICAL DEVICE

CROSS-REFERENCES TO RELATED APPLICATIONS

This application is a continuation of International Patent Application No. PCT/JP2021/031128 filed on Aug. 25, 2021, which claims priority to Japanese Patent Application No. 2020-142445 filed on Aug. 26, 2020, the entire content of both of which is incorporated herein by reference.

TECHNOLOGICAL FIELD

The present invention generally relates to a medical device that applies energy to a biological tissue.

BACKGROUND DISCUSSION

Chronic heart failure is one of known heart diseases. Chronic heart failure is broadly classified into a systolic heart failure and a diastolic heart failure, based on a cardiac function index. In a patient suffering from the diastolic heart failure, myocardial hypertrophy appears, and stiffness (hardness) increases, so that blood pressure increases in a left atrium, and a cardiac pumping function is degraded. Accordingly, the patient shows heart failure symptoms such as a pulmonary edema. In addition, there is another heart disease of a patient that shows the heart failure symptom because blood pressure increases on a right atrium side due to pulmonary hypertension, and the cardiac pumping function is degraded.

In recent years, shunt treatments have attracted attention in which, for the patients who suffer from heart failure, a shunt (through-hole) serving as an escape route for increased atrial pressure is formed in an atrial septum, thereby enabling heart failure symptoms to be alleviated. In the shunt treatment, the atrial septum is accessed using an intravenous approaching method, and the through-hole is formed to have a desired size. For example, a medical device disclosed in International Patent Application Publication No. 2019/85841 (WO2019/85841) is used as a medical device for performing the shunt treatment on the atrial septum.

SUMMARY

In the medical device described in International Patent Application Publication No. 2019/85841, an electrode portion is fixed to a recessed portion of an expansion body. Since a vicinity of a bottom portion of the recessed portion largely deforms when the expansion body is expanded or contracted in a radial direction, it is difficult to dispose the electrode portion in the vicinity of the bottom portion. When the electrode portion is disposed at a position away from the bottom portion of the recessed portion, there is a possibility that an edge portion of the through-hole of the atrial septum cannot be sufficiently heated and cauterized when high frequency energy is applied from the electrode portion to the through-hole. In a case where the edge portion of the through-hole is not sufficiently cauterized, a through-hole having a desired size cannot be obtained after the cauterization.

The medical device disclosed here includes an electrode portion provided in an expansion body, and the electrode portion can be disposed at a position close to a bottom portion of a recessed portion.

A medical device includes an expansion body configured to expand and contract in a radial direction; an elongated shaft portion including a distal portion that includes a proximal end fixing portion to which a proximal end of the expansion body is fixed; and a plurality of electrode assemblies extending from the proximal end fixing portion of the shaft portion along at least a part of the expansion body. The expansion body includes a recessed portion that is recessed radially inward and that defines a receiving space capable of receiving a biological tissue when the expansion body is expanded. The recessed portion includes a radially innermost bottom portion including a proximal side curved portion and a distal side curved portion, a proximal side upright portion extending radially outward from the proximal side curved portion, and a distal side upright portion extending radially outward from the distal side curved portion. Each of the plurality of electrode assemblies includes an electrode portion disposed along the expansion body from the proximal side upright portion or the distal side upright portion to the bottom portion so as to face the receiving space. The proximal side curved portion and the distal side curved portion are deformable so that proximal side curved portion and the distal side curved portion deform in response to expansion and contraction of the expansion body. The electrode portion is in a floating state with respect to the distal side curved portion and the proximal side curved portion.

In the medical device configured as described above, since the electrode portion is provided on the electrode assembly separate from the expansion body, the electrode portion can be disposed at a position close to the radially innermost bottom portion of the recessed portion. Since the electrode portion is not fixed to the proximal side curved portion and the distal side curved portion that deform in response to the expansion and contraction of the expansion body and is in a floating state, the electrode portion disposed at the position close to the bottom portion can be prevented from being damaged due to the deformation of the expansion body.

The expansion body may include a plurality of electrode engaging portions configured to engage each of the plurality of electrode assemblies with the expansion body. Each of the plurality of electrode assemblies may include an engaged portion that is engaged with a corresponding one of the electrode engaging portions. Each of the electrode engaging portions may be provided in at least one of the bottom portion, the proximal side upright portion, and the distal side upright portion. Accordingly, since each of the electrode assemblies is engaged and fixed to the plurality of electrode engaging portions of the expansion body, the electrode portion can be fixed to the expansion body so as not to be displaced.

The expansion body may include a proximal side expansion portion extending radially outward from the proximal end fixing portion of the shaft portion toward a distal direction. The proximal side expansion portion may include an outward curved portion whose distal end is connected to an outer end of the proximal side upright portion and which is curved in a convex shape outward in the radial direction. The proximal side upright portion may include a first through-hole penetrating the expansion body. At least one of the plurality of electrode assemblies may include an inner arrangement portion extending along an inner side of the expansion body from the distal portion of the shaft portion to the first through-hole through a vicinity of the outward curved portion of the proximal side expansion portion, and an outer arrangement portion extending along the expansion body from the first through-hole to at least the bottom portion so as to face the receiving space. The outward curved portion of the proximal side expansion portion may deform in response to the expansion and contraction of the expansion body. The inner arrangement portion may be separated from the outward curved portion of the proximal side expansion portion at least when the expansion body is expanded. The outer arrangement portion may be in a floating state with respect to the distal side curved portion and the proximal side curved portion. Accordingly, the electrode assembly can be prevented from interfering with the expansion body and being damaged.

The expansion body may include a second through-hole in the proximal side curved portion and a third through-hole in the distal side curved portion. The plurality of electrode engaging portions may include a first engaging portion between the second through-hole and the third through-hole of the bottom portion. The at least one of the plurality of electrode assemblies may include a first hook portion that is the engaged portion, the first hook portion being engaged with the first engaging portion by extending from an extension end of the outer arrangement portion, passing through the second through-hole, passing through the third through-hole from a radially inner side of the first engaging portion, and extending to an outer side of the expansion body. Accordingly, the electrode portion is disposed close to the bottom portion of the expansion body, the electrode assembly can follow the expansion and contraction of the expansion body, and the electrode assembly and the expansion body can be prevented from rubbing against each other and being damaged.

The expansion body may include a fourth through-hole in the distal side upright portion. The plurality of electrode engaging portions may include a second engaging portion formed from an edge portion of the fourth through-hole. The at least one of the plurality of electrode assemblies may include a second hook portion that is the engaged portion, the second hook portion being engaged with the second engaging portion by extending from an extension end of the first hook portion and passing through the fourth through-hole from the outer side to the inner side of the expansion body. Accordingly, the electrode assembly can be more strongly fixed to the expansion body, and the displacement of the electrode portion can be prevented.

The second hook portion may include a folded-back portion passing through the fourth through-hole and extending inside the expansion body toward the bottom portion. Accordingly, the electrode assembly can be more reliably fixed to the expansion body.

The at least one of the plurality of electrode assemblies may include a third hook portion that is the engaged portion, the third hook portion being engaged with the first engaging portion by extending from an extension end of the second hook portion, passing through the second through-hole from the inner side of the expansion body, and extending to the outer side of the expansion body. Accordingly, since the electrode assembly can be fixed to the expansion body at a portion further extending to the distal side of the electrode portion, the displacement of the electrode portion can be more effectively prevented.

The at least one of the plurality of electrode assemblies may include a first extension portion extending from an extension end of the third hook portion and extending between the outer arrangement portion and the proximal side upright portion toward the first through-hole. The medical device may further include a first cover configured to cover the proximal side upright portion and the first extension portion. Accordingly, when the expansion body is expanded or contracted, the electrode assembly can reliably follow movement of the proximal side upright portion, and the electrode assembly can be prevented from contacting an unintended location and being damaged.

The at least one of the plurality of electrode assemblies may include the electrode portion on the outer arrangement portion. The first cover may be sandwiched between the outer arrangement portion and the first extension portion. Accordingly, the electrode assembly can follow the expansion and contraction of the expansion body while exposing the electrode portion to an outside of the first cover.

The plurality of electrode engaging portions may include a third engaging portion formed from an edge portion of the first through-hole. The at least one of the plurality of electrode assemblies may include a first extension portion extending from an extension end of the third hook portion and extending between the outer arrangement portion and the proximal side upright portion toward the first through-hole, and a fourth hook portion that is the engaged portion, the fourth hook portion being engaged with the third engaging portion by extending from an extension end of the first extension portion and passing through the first through-hole. Accordingly, the electrode assembly can be more reliably fixed to the expansion body, and the displacement of the electrode portion can be prevented.

The fourth hook portion may include a crank-shaped portion extending from the extension end of the first extension portion, passing through the first through-hole, and extending along the inner side of the expansion body. Accordingly, the electrode assembly can be more reliably engaged with the expansion body.

The at least one of the plurality of electrode assemblies may include a second extension portion extending from an extension end of the crank-shaped portion and extending along the inner arrangement portion on a radially inner side of the inner arrangement portion. The medical device may further include a second cover configured to cover the second extension portion, the inner arrangement portion, and the proximal side expansion portion. Accordingly, since the electrode assembly can be moved to follow the proximal side expansion portion when the expansion body is expanded or contracted, the electrode assembly can be prevented from contacting an unintended location and being damaged.

The expansion body may include a second through-hole in the bottom portion. The plurality of electrode engaging portions may include a first engaging portion formed from an edge portion of the second through-hole. The at least one of the plurality of electrode assemblies may include a first hook portion that is the engaged portion, the first hook portion extending from an extension end of the outer arrangement portion, passing through the second through-hole, and extending to a radially inner side of the bottom portion. The first hook portion may include a wide portion that is wider than a portion of the first hook portion passing through the second through-hole and is engaged with the first engaging portion. Accordingly, the electrode portion is disposed close to the bottom portion of the expansion body, the electrode assembly can follow the expansion and contraction of the expansion body, and the electrode assembly and the expansion body can be prevented from rubbing against each other and being damaged.

The plurality of electrode engaging portions may include a second engaging portion formed from an edge portion of the third through-hole. The first hook portion may include a wide portion that is wider than a portion of the first hook portion passing through the third through-hole and is engaged with the second engaging portion. Accordingly, since the electrode assembly is engaged with the second engaging portion by the wide portion while being engaged with the first engaging portion, the electrode assembly can be more reliably fixed to the expansion body.

The expansion body may include a second through-hole in the proximal side curved portion and a fourth through-hole in the distal side upright portion. The plurality of electrode engaging portions may include a first engaging portion formed from an edge portion of the second through-hole and a second engaging portion formed from an edge portion of the fourth through-hole. The at least one of the plurality of electrode assemblies may include a first hook portion that is the engaged portion, the first hook portion being engaged with the first engaging portion by extending from an extension end of the outer arrangement portion, passing through the second through-hole, passing through the fourth through-hole from a radially inner side of the first engaging portion, and extending to an outer side of the expansion body. The first hook portion may include a wide portion that is wider than a portion of the first hook portion passing through the fourth through-hole and is engaged with the second engaging portion. Accordingly, since the electrode assembly can be fixed to the expansion body at a portion further extending to the distal side of the electrode portion, the displacement of the electrode portion can be more effectively prevented.

The expansion body may include a second through-hole in the distal side curved portion and a third through-hole in the proximal side curved portion. The plurality of electrode engaging portions may include a first engaging portion formed between the second through-hole and the third through-hole, and a fourth engaging portion formed from an edge portion of the first through-hole. The at least one of the plurality of electrode assemblies may include a first hook portion that is the engaged portion, the first hook portion being engaged with the first engaging portion by extending from an extension end of the outer arrangement portion, passing through the second through-hole, passing through the third through-hole from a radially inner side of the first engaging portion, and extending to an outer side of the expansion body, a first extension portion extending from an extension end of the first hook portion and extending between the outer arrangement portion and the proximal side upright portion toward the first through-hole, and a fourth hook portion that is the engaged portion, the fourth hook portion being engaged with the fourth engaging portion by extending from an extension end of the first extension portion and passing through the first through-hole. Accordingly, the electrode assembly can be engaged and fixed at two locations, that is, the first engaging portion and the fourth engaging portion, and the electrode portion can be fixed with a simple structure.

At least one of the plurality of electrode assemblies may be bonded and fixed to the expansion body at the proximal side upright portion or the distal side upright portion. Accordingly, the electrode portion can be fixed to the expansion body while making a portion of the electrode portion on the bottom portion side in a floating state with respect to the expansion body.

The expansion body may include a first through-hole in the distal side upright portion. At least one of the plurality of electrode assemblies may include an inner arrangement portion extending along the inner side of the expansion body from the distal portion of the shaft portion to the first through-hole of the distal side upright portion beyond the proximal side upright portion, and an outer arrangement portion folded back with respect to the inner arrangement portion and extending along the expansion body from the first through-hole to the bottom portion so as to face the receiving space. Accordingly, the electrode portion can be disposed on a distal side upright portion side with a simple structure.

The shaft portion may include a shaft extension portion extending inside the expansion body along a central axis of the expansion body from the proximal end fixing portion, and a distal end fixing portion to which a distal end of the expansion body is fixed. The expansion body may include a distal side expansion portion extending radially outward from the distal end fixing portion of the shaft portion toward a proximal direction. The distal side expansion portion may include an outward curved portion whose proximal end is connected to an outer end of the distal side upright portion and which is curved in a convex shape outward in the radial direction. The distal side upright portion may include a first through-hole. At least one of the plurality of electrode assemblies may include a shaft arrangement portion extending along the shaft extension portion from the proximal end fixing portion of the shaft portion to the distal end fixing portion, an inner arrangement portion extending along the inner side of the expansion body from an extension end of the shaft arrangement portion to the first through-hole through a vicinity of the outward curved portion of the distal side expansion portion, and an outer arrangement portion extending along the expansion body from the first through-hole to at least the bottom portion so as to face the receiving space. The outward curved portion of the distal side expansion portion may deform in response to the expansion and contraction of the expansion body. The inner arrangement portion may be separated from the outward curved portion of the distal side expansion portion at least when the expansion body is expanded. The outer arrangement portion may be in a floating state with respect to the distal side curved portion and the proximal side curved portion. Accordingly, the electrode assembly can be disposed while using the shaft portion, and the electrode assembly can be made less likely to interfere with the expansion and contraction of the expansion body.

The expansion body may include a second through-hole in the proximal side curved portion, a third through-hole in the distal side curved portion, and a fourth through-hole in the distal side upright portion. The plurality of electrode engaging portions may include a first engaging portion formed between the second through-hole and the third through-hole of the bottom portion, and a second engaging portion formed at an edge portion of the fourth through-hole. The at least one of the plurality of electrode assemblies may include a first hook portion that is the engaged portion, the first hook portion being engaged with the first engaging portion by extending from an extension end of the outer arrangement portion, passing through the second through-hole, passing through the third through-hole from a radially inner side of the first engaging portion, and extending to an outer side of the expansion body, and a second hook portion that is the engaged portion, the second hook portion being engaged with the second engaging portion by extending from an extension end of the first hook portion and passing through the fourth through-hole from the outer side to the inner side of the expansion body. The electrode portion may be disposed between the first hook portion and the second hook portion. Accordingly, when the electrode portion is disposed on a distal side upright portion side, the electrode assembly can be firmly engaged and fixed to the expansion body, and the displacement of the electrode portion can be prevented.

The expansion body may be formed of a mesh obtained by braiding many wires. At least one of the plurality of electrode assemblies may be inserted between the wires and engaged and fixed. Accordingly, the electrode assembly can also be fixed to the expansion body formed of a mesh, and the electrode portion can be disposed in a vicinity of the bottom portion of the recessed portion.

BRIEF DESCRIPTION OF THE DRAWINGS

FIG. 11 is a partial cross-sectional view of a vicinity of a recessed portion of an expansion body according to a first modification.

FIG. 12A is a partial cross-sectional view of a vicinity of a recessed portion of an expansion body according to a second modification, and FIG. 12B is an enlarged front view of a vicinity of a distal portion of an electrode assembly according to the second modification.

DETAILED DESCRIPTION

Figure 1:
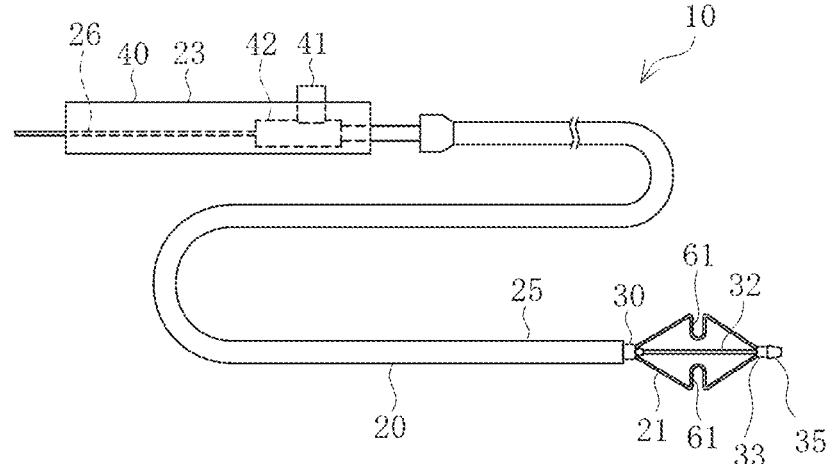
FIG. 1 is a diagram illustrating an overall configuration of a medical device according to an embodiment.

Hereinafter, an embodiment of an energy-applying medical device, representing an example of the new energy-applying medical device disclosed here, will be described with reference to the drawings. Dimensional ratios in the drawings may be exaggerated for convenience of description and may differ from actual ratios. In addition, in the present description, a side of a medical device 10 to be inserted into a body lumen is referred to as a "distal end" or a "distal side", and a hand side to be operated is referred to as a "proximal end" or a "proximal side".

A medical device in the following embodiment is configured such that a puncture hole Hh formed in an atrial septum HA of a heart H of a patient is expanded, and further, a maintenance treatment that maintains the expanded puncture hole Hh in an increased size can be performed.

As illustrated in FIG. 1, the medical device 10 according to the present embodiment includes an elongated shaft portion (shaft) 20, an expansion body 21 provided at a distal portion of the shaft portion 20, and an operation unit 23 provided at a proximal portion of the shaft portion 20. The expansion body 21 is provided with an electrode portion (electrode) 61 that is an energy transfer element for performing the maintenance treatment described above.

The shaft portion 20 includes a distal portion 30 including a proximal end fixing portion 31 to which a proximal end of the expansion body 21 is fixed and a distal end fixing portion 33 to which a distal end of the expansion body 21 is fixed. The distal portion 30 of the shaft portion 20 includes a shaft extension portion 32 extending inside the expansion body 21 from the proximal end fixing portion 31. The shaft portion 20 includes a housing sheath 25 provided on an outermost peripheral portion of the shaft portion 20. The expansion body 21 can move forward and backward in an axial direction with respect to the housing sheath 25. The housing sheath 25 can house the expansion body 21 therein while being moved to a distal side of the shaft portion 20. The expansion body 21 can be exposed when the housing sheath 25 is moved to a proximal side from a state of housing the expansion body 21.

The shaft portion 20 includes a pulling shaft 26. The pulling shaft 26 is provided from the proximal end of the shaft portion 20 to the shaft extension portion 32, and a distal portion of the pulling shaft 26 is fixed to a distal member 35.

The distal member 35 to which the distal portion of the pulling shaft 26 is fixed may not be fixed to the expansion body 21. Accordingly, the distal member 35 can pull the expansion body 21 in a compression direction. In addition, at the time of housing the expansion body 21 into the housing sheath 25, the expansion body 21 can be easily moved in an extension direction by separating the distal member 35 from the expansion body 21 to the distal side, and a housing property or housing ability can be improved.

The operation unit 23 includes a housing 40 to be gripped by an operator, an operation dial 41 that can be rotationally operated by the operator, and a conversion mechanism 42 that is operated in conjunction with the rotation of the operation dial 41. The pulling shaft 26 is held by the conversion mechanism 42 in an inside of the operation unit 23. The conversion mechanism 42 can move the held pulling shaft 26 forward and backward along the axial direction in conjunction with the rotation of the operation dial 41. As the conversion mechanism 42, for example, a rack and pinion mechanism can be used.

The shaft portion 20 is preferably formed of a material having a certain degree of flexibility. Examples of such a material include polyolefins such as polyethylene, polypropylene, polybutene, an ethylene-propylene copolymer, an ethylene-vinyl acetate copolymer, an ionomer, or a mixture of two or more thereof; soft polyvinyl chloride resin; polyamide; polyamide elastomer; polyester; polyester elastomer; polyurethane; a fluorine resin such as polytetrafluoroethylene; polyimide; PEEK; silicone rubber; and latex rubber.

The pulling shaft 26 can be formed, for example, by coating an elongated wire made of a metallic material such as stainless steel or a superelastic alloy such as a nickel-titanium alloy or a copper-zinc alloy, or made of a resin material having a relatively high rigidity with a resin material such as polyvinyl chloride, polyethylene, polypropylene or ethylene-propylene copolymer.

The distal member 35 can be made of, for example, a polymeric material such as polyolefin, polyvinyl chloride, polyamide, polyamide elastomer, polyurethane, polyurethane elastomer, polyimide or fluororesin or a mixture thereof, or a multilayer tube of two or more kinds of polymeric materials.

Figure 2:
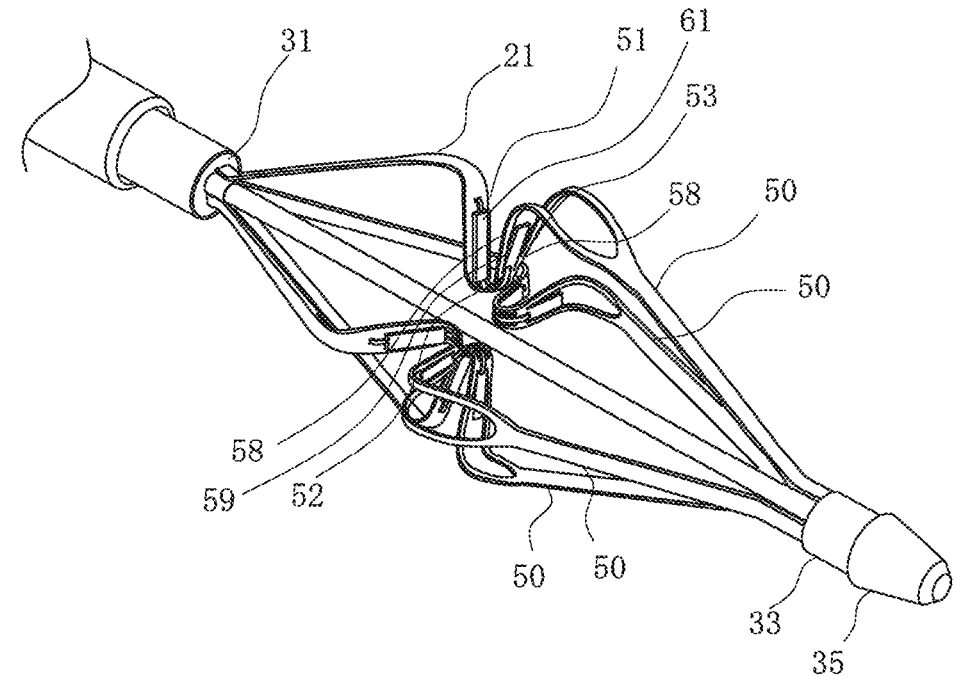
FIG. 2 is an enlarged perspective view of a vicinity of an expansion body.

The expansion body 21 will be described in more detail. As illustrated in FIG. 2, the expansion body 21 includes a plurality of wire portions 50 arranged or spaced apart in a circumferential direction. In the present embodiment, four wire portions 50 are provided in the circumferential direction. Each of the wire portions 50 can expand and contract in a radial direction. A proximal end of each of the wire portions 50 is fixed to the proximal end fixing portion 31, and the wire portions 50 extend from the proximal end fixing portion 31 to the distal side. A distal end of each of the wire portions 50 is fixed to the distal end fixing portion 33, and the wire portions 50 extend from the distal end fixing portion 33 to the proximal side. The wire portions 50 are inclined so as to increase in the radial outward direction (i.e., be spaced farther and farther from the shaft extension portion 32) from both end portions in the axial direction toward a center portion. In addition, the wire portions 50 each include a recessed portion 51 that is recessed radially inward of the expansion body 21 at the central portion in the axial direction. A radially innermost portion of the recessed portion 51 is a bottom portion 52.

Figure 3:
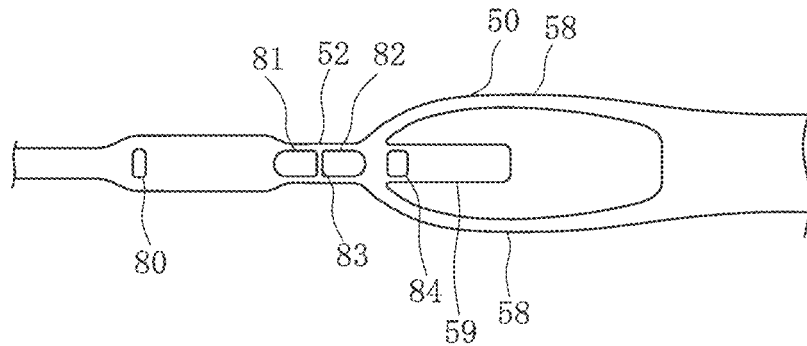
FIG. 3 is a front view illustrating a state in which one wire portion is flattened.

As illustrated in FIG. 3, the wire portions 50 each include a second through-hole 81 and a third through-hole 82 in a portion serving as the bottom portion 52, and includes a first engaging portion 83 serving as an electrode engaging portion between the second through-hole 81 and the third through-hole 82. A first through-hole 80 is formed on the proximal side of the second through-hole 81, and a fourth through-hole 84 is formed on the distal side of the third through-hole 82. The wire portions 50 are each configured so that a distal side of the bottom portion 52 includes a slit shape center portion (elongated center through hole) in a width direction, and includes outer edge portions 58 on both sides and a back support portion 59 on the center portion.

The wire portions 50 forming the expansion body 21 each have, for example, a flat plate shape cut out from a cylinder. That is the expansion body 21 can be considered as a cylinder in which circumferentially spaced-apart portions are cut-out, leaving the circumferentially spaced-apart wire portions 50. The wire forming the expansion body 21 can have a thickness of 50 μm to 500 μm and a width of 0.3 mm to 2.0 mm. However, the wire may have a dimension outside this range. In addition, the wire portions 50 may have a circular cross-sectional shape or a cross-sectional shape other than the circular cross-sectional shape.

Figure 4A:
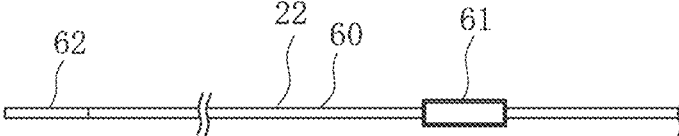
FIG. 4A is a front view of an electrode assembly.
Figure 4B:
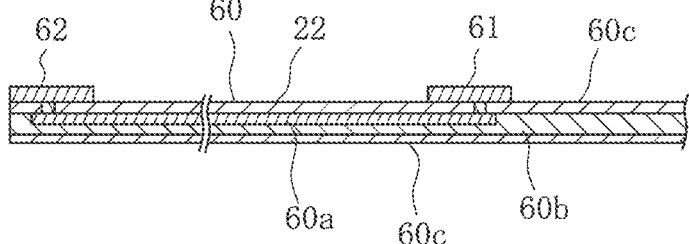
FIG. 4B is a cross-sectional view of the electrode assembly.

An electrode assembly 22 separate from the expansion body 21 is attached to the expansion body 21. More specifically, each of the wire portions 50 includes one of the electrode assemblies 22. The description below referring to the electrode assembly 22 should be understood to apply to each of the electrode assemblies 22, and the description of the way in which the electrode assembly 22 is mounted on or fixed to the wire portion 50 applies to each of the electrode assembly 22/wire portion 50 combinations. As illustrated in FIG. 4A, the electrode assembly 22 includes an elongated wiring portion 60, the electrode portion 61 provided in an intermediate portion in a length direction of the wiring portion 60, and a connection portion 62 provided at a proximal portion of the wiring portion 60. As illustrated in FIG. 4B, the wiring portion 60 includes an electric wire portion 60a having conductivity. The electric wire portion 60a, the electrode portion 61, and the connection portion 62 can be made of a metal material. The electric wire portion 60a is embedded in an adhesive layer 60b sandwiched between insulating layers 60c provided on both surfaces of the wiring portion 60 in a thickness direction. The electrode portion 61 is provided so as to be exposed on a surface of the insulating layer 60c, and is electrically connected to the electric wire portion 60a. In addition, the connection portion 62 is a portion that electrically connects the electrode assembly 22 to a connection line (not illustrated) provided on the proximal side of the medical device 1, and similarly to the electrode portion 61, is exposed on the surface of the insulating layer 60c and electrically connected to the electric wire portion 60a.

The electrode portion 61 is implemented by, for example, a bipolar electrode that receives electric energy from an energy supply device (not illustrated), which is an external device. In this case, energization is performed among the electrode portions 61 disposed on the wire portions 50. The electrode portion 61 and the energy supply device are connected by a conducting wire (not illustrated) covered with an insulating covering material. The conducting wire is led out to the outside through the shaft portion 20 and the operation unit 23, and is connected to the energy supply device.

Alternatively, the electrode portion 61 may be implemented by a monopolar electrode. In this case, energization is performed from a counter electrode plate prepared outside a body. In addition, instead of the electrode portion 61, a heat generating element (electrode tip) that receives high-frequency electric energy from the energy supply device and generates heat may be used. In this case, energization is performed among the heat generating elements disposed in the wire portions 50. Further, the electrode portion 61 may include an energy transfer element capable of applying energy to the puncture hole Hh, such as an element that performs heating or cooling by using microwave energy, ultrasound energy, coherent light such as laser, a heated fluid, a cooled fluid, or a chemical medium, an element that generates frictional heat, or a heater including an electric wire, and a specific form thereof is not specially limited.

The wire portions 50 can be made of a metal material. As the metal material, for example, a titanium-based (Ti—Ni, Ti—Pd, Ti—Nb—Sn, etc.) alloy, a copper-based alloy, stainless steel, β titanium steel, or a Co—Cr alloy can be used. An alloy having a spring property such as a nickel titanium alloy may be more preferably used. However, a material for the wire portions 50 is not limited thereto, and the wire portions 50 may be made of other materials.

Figure 5:
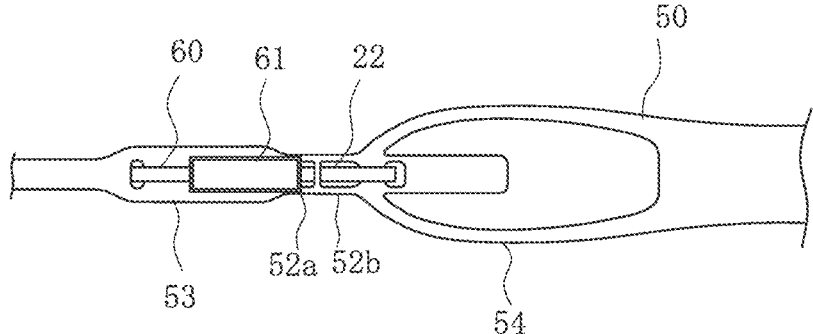
FIG. 5 is a front view illustrating a state in which the electrode assembly is combined with the wire portion.
Figure 6:
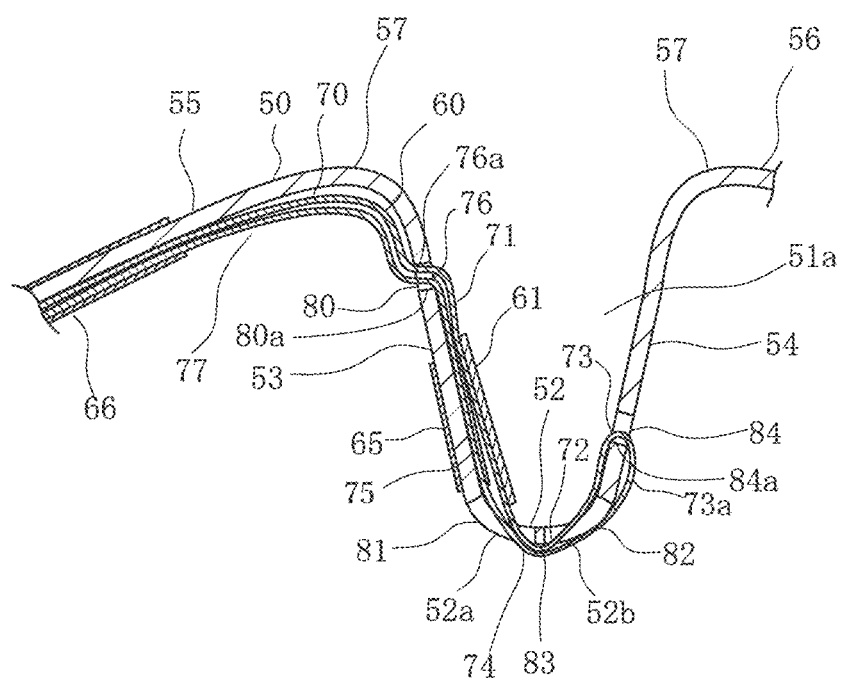
FIG. 6 is a partial cross-sectional view of a vicinity of a recessed portion of the expansion body.

As illustrated in FIGS. 5 and 6, the electrode assembly 22 is fixed along a surface of the wire portion 50 by engaging and hooking the wiring portion 60 with a plurality of electrode engaging portions of the expansion body 21. The wire portion 50 includes the recessed portion 51 that is recessed radially inward and defines a receiving space 51a capable of receiving a biological tissue when the expansion body 21 is expanded. The wire portion 50 includes a proximal side curved portion 52a that is a proximal side portion of the bottom portion 52, which is on a radially innermost side of the recessed portion 51, and a distal side curved portion 52b that is a distal side portion of the bottom portion 52. The wire portion 50 includes a proximal side upright portion 53 extending radially outward from the proximal side curved portion 52a toward the proximal side, and a distal side upright portion 54 extending radially outward from the distal side curved portion 52b toward the distal side. In addition, the wire portion 50 includes a proximal side expansion portion 55 extending radially outward from the proximal end fixing portion 31 of the shaft portion 20 toward the distal side, and a distal side expansion portion 56 extending radially outward from the distal end fixing portion 33 of the shaft portion 20 toward the proximal side. The proximal side expansion portion 55 includes an outward curved portion 57 whose distal end is connected to an outer end of the proximal side upright portion 53, which is curved in a convex shape outward in the radial direction, and which deforms in response to expansion and contraction of the expansion body 21. Further, the distal side expansion portion 56 includes an outward curved portion 57 whose proximal end is connected to an outer end of the distal side upright portion 54, is curved in a convex shape outward in the radial direction, and deforms in response to the expansion and contraction of the expansion body 21.

The proximal side upright portion 53 includes the first through-hole 80, and a third engaging portion 80a serving as an electrode engaging portion that engages the electrode assembly 22 is formed by an edge portion of the proximal side upright portion 53. The proximal side curved portion 52a includes the second through-hole 81, the distal side curved portion 52b includes the third through-hole 82, and the first engaging portion 83 serving as an electrode engaging portion is formed between the second through-hole 81 and the third through-hole 82. The first engaging portion 83 has a form in which both end portions in the width direction are bridged in the bottom portion 52 of the wire portion 50. The distal side upright portion 54 includes the fourth through-hole 84, and a second engaging portion 84a serving as an electrode engaging portion is formed by an edge portion of the distal side upright portion 54.

The electrode assembly 22 includes an inner arrangement portion 70 extending along an inner side of the expansion body 21 from the distal portion 30 of the shaft portion 20 toward a distal direction to the first through-hole 80 through a vicinity of the outward curved portion 57 of the proximal side expansion portion 55. The inner arrangement portion 70 is separated from the outward curved portion 57 of the wire portion 50 when the expansion body 21 is expanded. Therefore, the electrode assembly 22 can be prevented from being damaged even when the outward curved portion 57 deforms when the expansion body 21 is expanded or contracted.

The electrode assembly 22 includes an outer arrangement portion 71 extending from the first through-hole 80 to the bottom portion 52 of the recessed portion 51 so as to face the receiving space 51a along the expansion body 21. The electrode portion 61 is disposed on the outer arrangement portion 71 and faces the receiving space 51a.

The electrode assembly 22 includes a first hook portion 72 that is hooked and engaged with the first engaging portion 83 by extending from an extension end of the outer arrangement portion 71, passing through the second through-hole 81, passing through the third through-hole 82 from a radially inner side of the first engaging portion 83, and extending to an outer side of the expansion body 21. The first hook portion 72 functions as an engaged portion that is engaged with the first engaging portion 83, which is an electrode engaging portion. Here, in the present description, the "extension end" indicates an end in an extending direction when each of the plurality of electrode assemblies 22 extends from the distal portion of the shaft portion 20 or the distal portion of the expansion body 21 along the expansion body 21. One of the plurality of electrode assemblies 22 may extend from the distal portion of the expansion body 21, and the other electrode assembly 22 may extend from the distal portion of the shaft portion 20.

Since the electrode portion 61 is provided on the electrode assembly 22 that is separate from the wire portion 50 forming the expansion body 21, the electrode portion 61 can be disposed in a position close to the radially innermost bottom portion 52 of the recessed portion 51. In addition, since the electrode portion 61 is not fixed to the proximal side curved portion 52a and the distal side curved portion 52b that are deformed by the expansion and contraction of the expansion body 21 and is in a floating state (i.e., the electrode portion 61 is movable relative to the proximal side curved portion 52a and the distal side curved portion 52b of the expansion body), the electrode portion 61 can be prevented from being damaged due to the deformation of the expansion body 21.

The electrode assembly 22 includes a second hook portion 73 that is engaged with the second engaging portion 84a by extending from an extension end of the first hook portion 72 and passing through the fourth through-hole 84 from the outer side to the inner side of the expansion body 21. The second hook portion 73 functions as an engaged portion that is engaged with the second engaging portion 84a, which is an electrode engaging portion. The second hook portion 73 includes a folded-back portion 73a passing through the fourth through-hole 84 and extending toward the bottom portion 52 inside the expansion body 21. The electrode assembly 22 is reliably fixed to the wire portion 50 by the second hook portion 73, and displacement of the electrode portion 61 can be prevented.

The electrode assembly 22 includes a third hook portion 74 that is engaged with the first engaging portion 83 by extending from an extension end of the second hook portion 73, passing through the second through-hole 81 from the inner side of the expansion body 21, and extending to the outer side of the expansion body 21. The third hook portion 74 functions as an engaged portion that is engaged with the first engaging portion 83, which is an electrode engaging portion. Further, the electrode assembly 22 includes a first extension portion 75 extending from an extension end of the third hook portion 74 and extending between the outer arrangement portion 71 and the proximal side upright portion 53 toward the first through-hole 80. The proximal side upright portion 53 and the first extension portion 84 are covered with a first cover 65. A heat-shrinkable tube or the like can be used as the first cover 65.

The first cover 65 enables the electrode assembly 22 to reliably follow movement of the proximal side upright portion 53 when the expansion body 21 is expanded or contracted. Accordingly, the electrode assembly 22 can be prevented from contacting an unintended location and being damaged. In addition, since a portion of the electrode assembly 22 covered with the first cover 65 is slidable in a length direction, a local excessive deformation force can be prevented from being applied to the electrode assembly 22 when the expansion body 21 is expanded or contracted.

The electrode assembly 22 includes a fourth hook portion 76 that is engaged with the third engaging portion 80a by extending from an extension end of the first extension portion 84 and passing through the first through-hole 80. The fourth hook portion 76 functions as an engaged portion that is engaged with the third engaging portion 80a, which is an electrode engaging portion. The fourth hook portion 76 includes a crank-shaped portion 76a extending from the extension end of the first extension portion 84, passing through the first through-hole 80, and extending along the inner side of the expansion body 21.

The electrode assembly 22 includes a second extension portion 77 extending from an extension end of the crank-shaped portion 76a and extending along the inner arrangement portion 70 on a radially inner side of the inner arrangement portion 70. The second extension portion 77, the inner arrangement portion 70, and the proximal side expansion portion 55 are covered with a second cover 66. A heat-shrinkable tube or the like can be used as the second cover 66. Similarly to the first cover 65, the second cover 66 can also prevent the electrode assembly 22 from contacting an unintended location, and prevent a local excessive deformation force from being applied to the electrode assembly 22 when the expansion body 21 is expanded or contracted.

Figure 7:
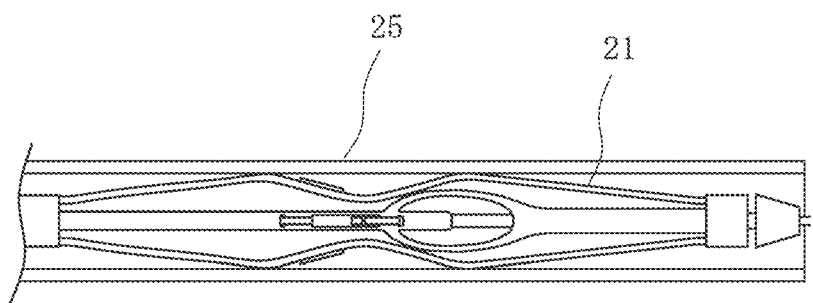
FIG. 7 is a view illustrating the expansion body housed in a housing sheath.

As illustrated in FIG. 7, the expansion body 21 housed in the housing sheath 25 is contracted in the radial direction. When the expansion body 21 and the housing sheath 25 move in the axial direction relative to each other, the expansion body 21 is exposed to the outside of the housing sheath 25 and expands in the radial direction.

Figure 8:
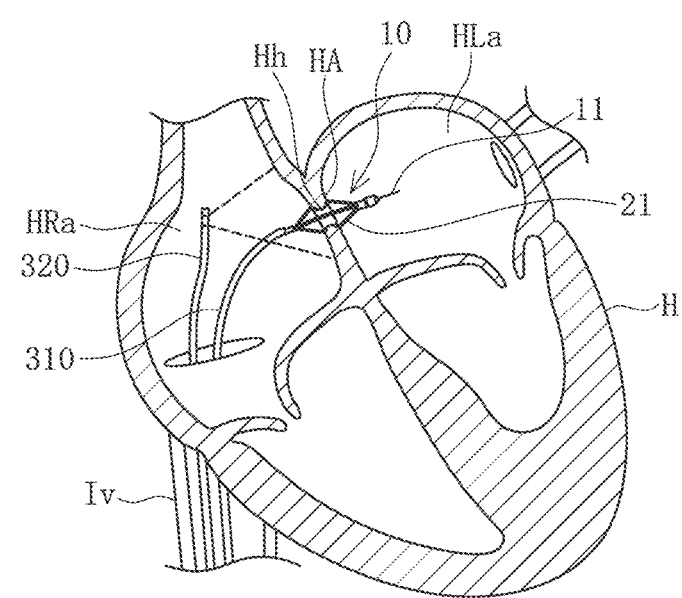
FIG. 8 is an explanatory view schematically illustrating a state in which the expansion body is disposed in an atrial septum, the medical device being in a plan view, and a biological tissue being in a cross-sectional view.

A treatment method using the medical device 10 will be described. The treatment method according to the present embodiment is performed on a patient suffering from heart failure (left heart failure). More specifically, as illustrated in FIG. 8, the treatment method is performed on a patient suffering from a chronic heart failure, who has high blood pressure in a left atrium HLa due to myocardial hypertrophy appearing in a left ventricle of the heart H and increased stiffness (hardness).

The treatment method according to the present embodiment includes a step (S1) of forming the puncture hole Hh in the atrial septum HA, a step (S2) of disposing the expansion body 21 in the puncture hole Hh, a step (S3) of expanding a diameter of the puncture hole Hh by the expansion body 21, a step (S4) of confirming hemodynamics in a vicinity of the puncture hole Hh, a step (S5) of performing the maintenance treatment for maintaining the size of the puncture hole Hh, and a step (S6) of confirming the hemodynamics in the vicinity of the puncture hole Hh after the maintenance treatment is performed.

At the time of forming the puncture hole Hh, the operator delivers an introducer 310 in which a guiding sheath and a dilator are combined to a vicinity of the atrial septum HA. For example, the introducer 310 can be delivered to a right atrium HRa via an inferior vena cava Iv. In addition, the introducer can be delivered using a guide wire 11. The operator can insert the guide wire 11 into the dilator and deliver the introducer along the guide wire 11. The introducer and the guide wire 11 can be inserted into a living body using a known method such as using an introducer for blood vessel introduction.

In step S1, the operator causes a puncture device (not illustrated) to penetrate from a right atrium HRa side toward a left atrium HLa side to form the puncture hole Hh in the atrial septum HRa. For example, a device such as a wire having a sharp distal end can be used as the puncture device. The puncture device is inserted into the dilator and delivered to the atrial septum HA. After the guide wire 11 is removed from the dilator, the puncture device can be delivered to the atrial septum HA in place of the guide wire 11.

In step S2, first, the medical device 10 is delivered to the vicinity of the atrial septum HA along the guide wire 11 inserted in advance. At this time, the distal portion of the medical device 10 penetrates the atrial septum HA (i.e., passes through the puncture in the atrial septum HRa) and reaches the left atrium HLa. In addition, when the medical device 10 is inserted, the expansion body 21 is in a state of being housed in the housing sheath 25.

Figure 9:
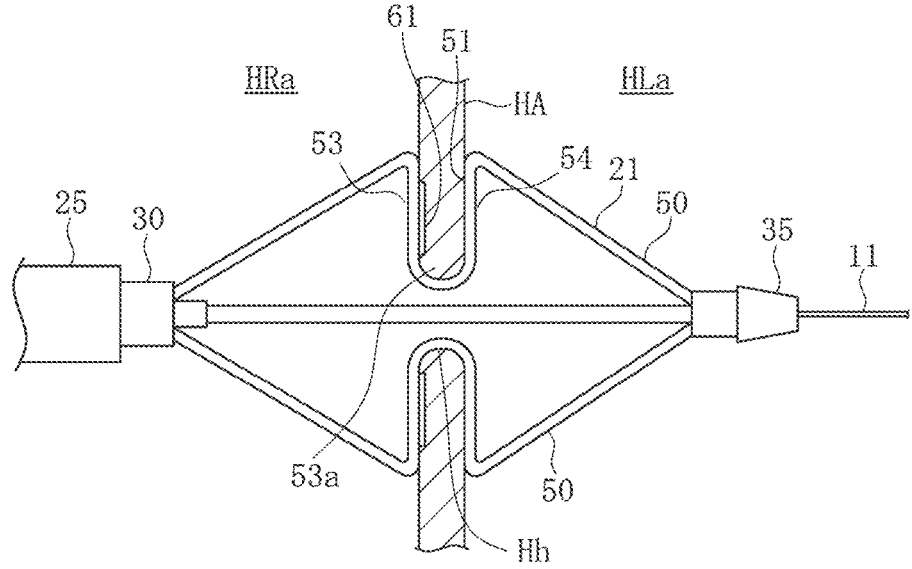
FIG. 9 is an enlarged view of a vicinity of the expansion body in FIG. 8.

Next, as illustrated in FIG. 9, the expansion body 21 is exposed by moving the housing sheath 25 to the proximal side. Accordingly, the expansion body 21 is expanded in diameter, the recessed portion 51 is disposed in the puncture hole Hh of the atrial septum HA, and a biological tissue surrounding the puncture hole Hh is received in the receiving space 51a. Accordingly, the biological tissue is sandwiched between the proximal side upright portion 53 on which the electrode portion 61 is provided and the distal side upright portion 54.

Figure 10:
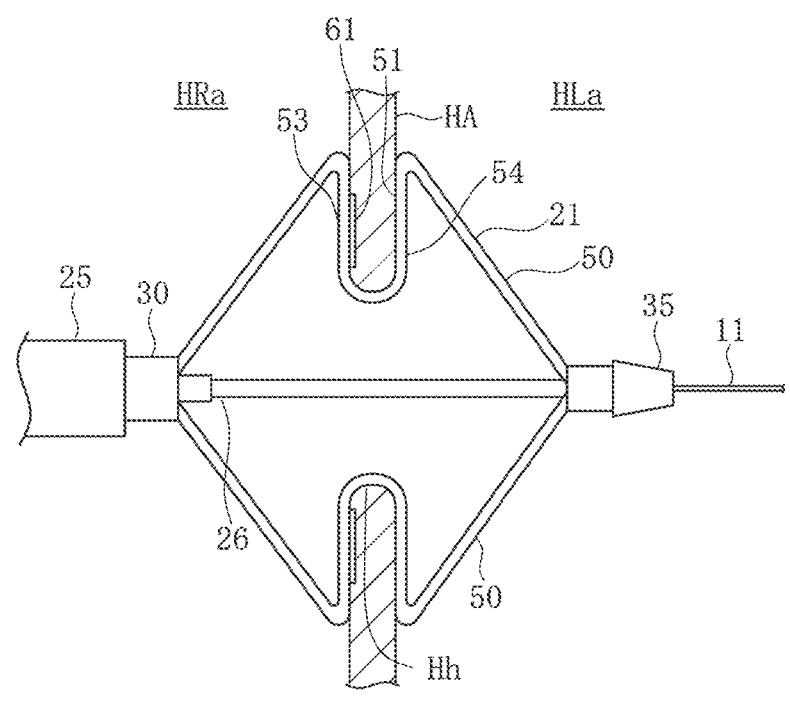
FIG. 10 is an explanatory view illustrating a state in which the expansion body is expanded in diameter in the atrial septum from the state in FIG. 8.

In step S3, the operator operates the operation unit 23 in a state in which the biological tissue is received in the receiving space 51a, and moves the pulling shaft 26 to the proximal side. Accordingly, as illustrated in FIG. 10, the expansion body 21 is further expanded in the radial direction, and the puncture hole Hh is expanded in the radial direction.

After the puncture hole Hh is expanded, the hemodynamics is confirmed in step S4. As illustrated in FIG. 8, the operator delivers a hemodynamics confirming device 320 to the right atrium HRa via the inferior vena cava Iv. For example, a known echo catheter can be used as the hemodynamics confirming device 320. The operator can display an echo image acquired by the hemodynamics confirming device 320 on a display device such as a display, and confirm a blood volume passing through the puncture hole Hh based on a display result.

Next, in step S5, the operator performs the maintenance treatment in order to maintain the size of the puncture hole Hh. In the maintenance treatment, by applying high-frequency energy to the edge portion of the puncture hole Hh by the electrode portion 61, an edge portion of the puncture hole Hh is cauterized (heated and cauterized) by the high-frequency energy.

When the biological tissue in a vicinity of the edge portion of the puncture hole Hh is cauterized by the electrode portion 61, a degenerated portion having a degenerated biological tissue is formed in the vicinity of the edge portion. Since the biological tissue in the degenerated portion loses elasticity, the puncture hole Hh can maintain a shape when being expanded by the expansion body 21.

After the maintenance treatment, the hemodynamics is confirmed again in step S6, and when a blood volume passing through the puncture hole Hh is a desired volume, the operator contracts the expansion body 21 in diameter, stores the expansion body 21 in the housing sheath 25, and then removes the expansion body 21 from the puncture hole Hh. Further, the entire medical device 10 is removed to the outside of the living body, and the treatment is ended.

Next, modifications of the expansion body and the electrode assembly will be described. As illustrated in FIG. 11, a wire portion 101 of an expansion body 100 according to a first modification includes a proximal side curved portion 103a and a distal side curved portion 103b at a bottom portion 103 of a recessed portion 102. A second through-hole 121 is formed in the distal side curved portion 103b, a third through-hole 122 is formed in the proximal side curved portion 103a, and a first engaging portion 123 is formed between the second through-hole 121 and the third through-hole 122. The first engaging portion 123 is disposed slightly closer to the proximal side at the bottom portion 103 of the recessed portion 102. A first through-hole 120 is formed in a proximal side upright portion 104 of the wire portion 101.

An electrode assembly 110 includes an inner arrangement portion 113 on the proximal side of the first through-hole 120 and an outer arrangement portion 114 on the distal side of the first through-hole 120. An electrode portion 112 is disposed on the outer arrangement portion 114 so as to face a receiving space 102b. The electrode assembly 110 includes a first hook portion 115 that is engaged with the first engaging portion 123 by extending from an extension end of the outer arrangement portion 114, passing through the second through-hole 121 of the distal side curved portion 103b passing through the third through-hole 122 of the proximal side curved portion 103a from a radially inner side of the first engaging portion 123, and extending to an outer side of the expansion body 100. Since the first engaging portion 123 is disposed closer to the proximal side of the bottom portion 103, the electrode portion 112 can be disposed along the proximal side upright portion 104.

A wiring portion 111 includes a first extension portion 116 extending from an extension end of the first hook portion 115 and extending between the outer arrangement portion 114 and the proximal side upright portion 104 toward the first through-hole 120. Further, the wiring portion 111 includes a fourth hook portion 117 that extends from an extension end of the first extension portion 116 and passes through the first through-hole 120 to engage with a fourth engaging portion 120a formed at an edge portion of the first through-hole 120. In this manner, the electrode assembly 110 may be folded back at the first engaging portion 123 formed at the bottom portion 103 of the recessed portion 102.

Next, an expansion body 130 and an electrode assembly 140 according to a second modification will be described. As illustrated in FIG. 12A, a wire portion 131 of the expansion body 130 includes a recessed portion 132. A second through-hole 151 is formed in a bottom portion 133 of the recessed portion 132. A first engaging portion 151a is formed at an edge portion of the second through-hole 151.

The electrode assembly 140 includes an inner arrangement portion 143 on a proximal side of a first through-hole 150 and an outer arrangement portion 144 on a distal side of the first through-hole 150. An electrode portion 142 is disposed on the outer arrangement portion 144 so as to face a receiving space 132a. A wiring portion 141 includes a first hook portion 145 that extends from an extension end of the outer arrangement portion 114, passes through the second through-hole 151, and extends to a radially inner side of the bottom portion 133. As illustrated in (b) of FIG. 12, the first hook portion 145 includes a wide portion 145a that is wider than a passing portion 145b of the first hook portion 145 passing through the second through-hole 151 and is engaged with the first engaging portion 151a. When the wide portion 145a is hooked and engaged with the first engaging portion 151a, the first hook portion 145 is fixed to the wire portion 131. In this manner, the electrode assembly 140 may use the wide portion 145a provided at the distal portion as an engaged portion.

Figure 13:
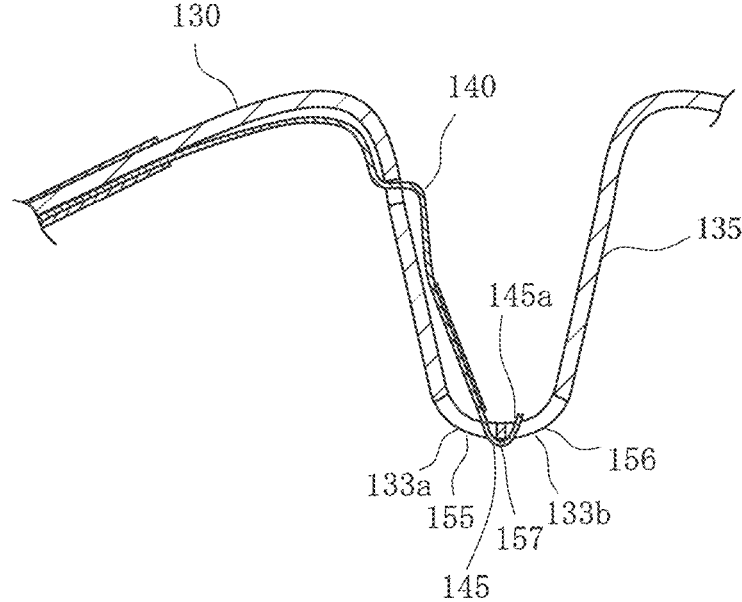
FIG. 13 is a partial cross-sectional view of the vicinity of the recessed portion of the expansion body in which a fixing structure of a first hook portion is changed from the state in FIG. 11.

A fixing structure of the first hook portion 145 including the wide portion 145a may be in another form. As illustrated in FIG. 13, the expansion body 130 includes a second through-hole 155 in a proximal side curved portion 133a and a third through-hole 156 in a distal side curved portion 133b, and a first engaging portion 157 is formed between the second through-hole 155 and the third through-hole 156. The first hook portion 145 is engaged with the first engaging portion 157 by extending from an extension end of the outer arrangement portion 144, passing through the second through-hole 155, passing through the third through-hole 156 from a radially inner side of the first engaging portion 157, and extending to an outer side of the expansion body 130. In addition, the wide portion 145a of the first hook portion 145 is hooked and engaged with a second engaging portion 156a formed at an edge portion of the third through-hole 156.

Figure 14:
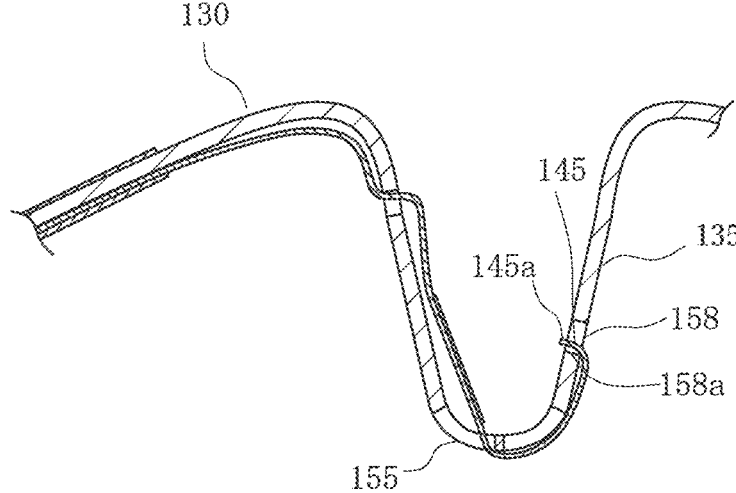
FIG. 14 is a partial cross-sectional view of the vicinity of the recessed portion of the expansion body in which a fixing structure of a first hook portion is changed from the state in FIG. 11.

As illustrated in FIG. 14, the expansion body 130 may include a fourth through-hole 158 in a distal side upright portion 132, and a second engaging portion 158a may be formed at an edge portion of the fourth through-hole 158. The first hook portion 145 passing through the second through-hole 155 may be engaged with the second engaging portion 158a at the wide portion 145a by extending to the fourth through-hole 158.

Figure 15:
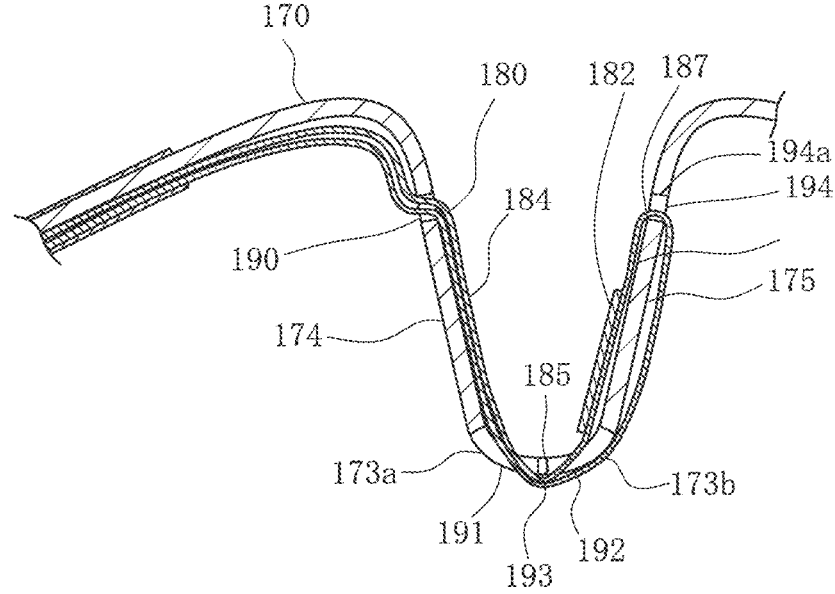
FIG. 15 is a partial cross-sectional view of a vicinity of a recessed portion of an expansion body according to a third modification.

Next, an expansion body 170 and an electrode assembly 180 according to a third modification will be described. As illustrated in FIG. 15, a configuration of the expansion body 170 is similar to that in FIG. 6, and the expansion body 170 includes a first through-hole 190 in a proximal side upright portion 174, a second through-hole 191 in a proximal side curved portion 173a, a third through-hole 192 in a distal side curved portion 173b, and a fourth through-hole 194 in a distal side upright portion 175. The expansion body 170 includes, as electrode engaging portions, a first engaging portion 193 formed between the second through-hole 191 and the third through-hole 192 of a bottom portion 173, and a second engaging portion 194a formed at an edge portion of the fourth through-hole 194.

The electrode assembly 180 includes a first hook portion 185 that is engaged with the first engaging portion 193 by extending from an extension end of an outer arrangement portion 184, passing through the second through-hole 191, passing through the third through-hole 192 from a radially inner side of the first engaging portion 193, and extending to an outer side of the expansion body 170. In addition, the electrode assembly 180 includes a second hook portion 187 that is engaged with the second engaging portion 194a by extending from an extension end of the first hook portion 185 and passing through the fourth through-hole 194 from an outer side to an inner side of the expansion body 170. An electrode portion 182 is disposed between the first hook portion 185 and the second hook portion 187. Therefore, the electrode portion 182 is disposed along the distal side upright portion 175 of a recessed portion 172. In this manner, the electrode portion 182 may be disposed on a distal side of the recessed portion 172.

Figure 16:
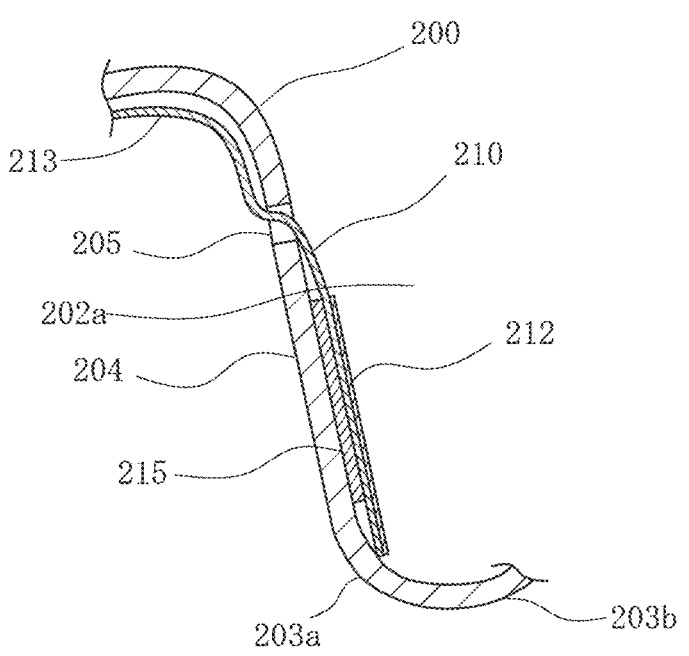
FIG. 16 is a partial cross-sectional view of a vicinity of a recessed portion of an expansion body according to a fourth modification.

Next, an expansion body 200 and an electrode assembly 210 according to a fourth modification will be described. As illustrated in FIG. 16, the expansion body 200 includes a first through-hole 205 in a proximal side upright portion 204. The electrode assembly 210 includes an inner arrangement portion 213 and an outer arrangement portion 214 with the first through-hole 205 located therebetween, and the outer arrangement portion 214 is disposed along the proximal side upright portion 204. An electrode portion 212 is disposed on the outer arrangement portion 214. The electrode portion 212 faces a receiving space 202a, and a back side of the electrode portion 212 is bonded and fixed to the expansion body 200 by a bonding portion 215. The bonding portion 215 is provided in a radially outer region of the electrode portion 212, and does not reach a proximal side curved portion 203a and a distal side curved portion 203b of the expansion body 200. Therefore, the outer arrangement portion 214 on which the electrode portion 212 is disposed is in a floating state with respect to the proximal side curved portion 203a and the distal side curved portion 203b. In this manner, the electrode assembly 200 may be fixed by bonding, and in this case, the electrode portion 212 can extend to a vicinity of a bottom portion 203 by forming the bonding portion 215 such that the electrode portion 212 is in a floating state with respect to the proximal side curved portion 203a and the distal side curved portion 203b.

Figure 17:
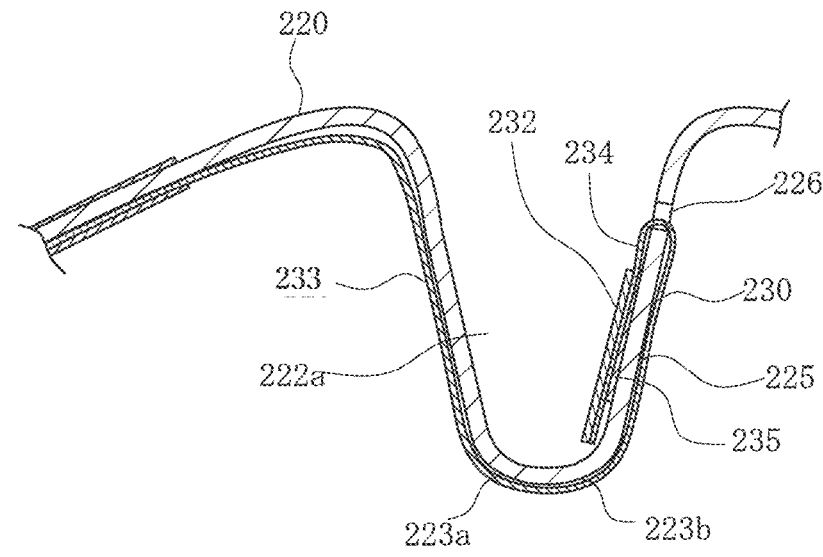
FIG. 17 is a partial cross-sectional view of a vicinity of a recessed portion of an expansion body according to a fifth modification.

Next, an expansion body 220 and an electrode assembly 230 according to a fifth modification will be described. As illustrated in FIG. 17, the expansion body 220 includes a first through-hole 226 in a distal side upright portion 225. The electrode assembly 230 includes an inner arrangement portion 233 extending from the distal portion 30 of the shaft portion 20 to the first through-hole 226 of the distal side upright portion 225 passing a proximal side upright portion 224 along an inner side of the expansion body 220. In addition, the expansion body 220 includes an outer arrangement portion 234 extending from the first through-hole 226 to a bottom portion 223 along the expansion body 220 so as to be folded back with respect to the inner arrangement portion 233 and face a receiving space 222a. An electrode portion 232 is disposed along the outer arrangement portion 234, and is fixed to the outer arrangement portion 234 by a bonding portion 235. The bonding portion 235 does not reach to a proximal side curved portion 223a and a distal side curved portion 223b, and a region of the outer arrangement portion 234 in which the electrode portion 232 is disposed on a bottom portion 223 side is in a floating state with respect to the proximal side curved portion 223a and the distal side curved portion 223b. In this manner, the inner arrangement portion 233 may be long, and the electrode portion 232 may be disposed along the distal side upright portion 225. In this case, the fixation of the electrode assembly 230 is not limited to bonding, and the electrode assembly 230 may be fixed by the plurality of electrode engaging portions described above.

Figure 18:
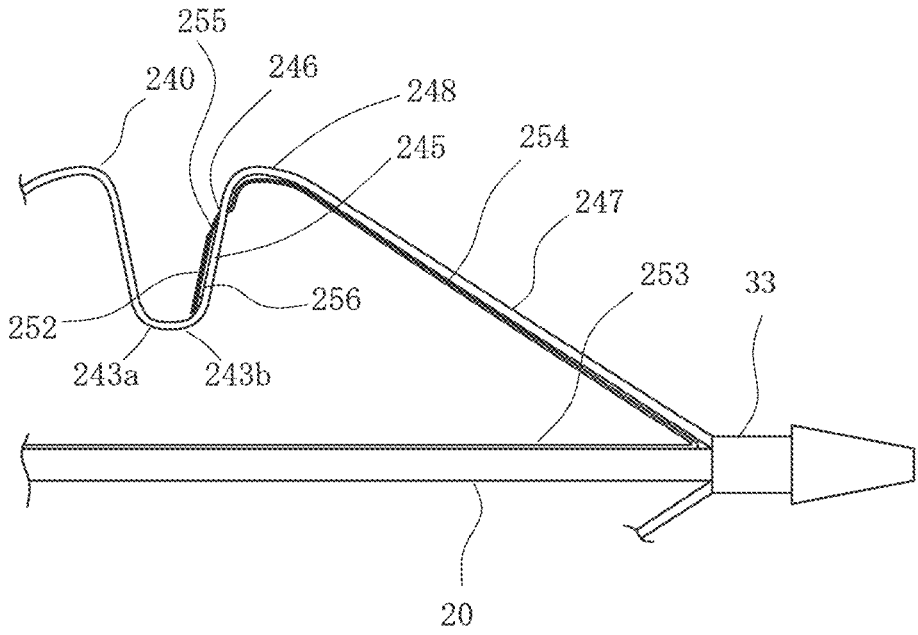
FIG. 18 is a partially enlarged view of an expansion body according to a sixth modification.

Next, an expansion body 240 and an electrode assembly 250 according to a sixth modification will be described. As illustrated in FIG. 18, a distal side upright portion 245 of the expansion body 240 includes a first through-hole 246. The electrode assembly 250 includes a shaft arrangement portion 253 extending from the proximal end fixing portion 31 of the shaft portion 20 to the distal end fixing portion 33 along the shaft extension portion 32. The electrode assembly 250 includes an inner arrangement portion 254 extending along an inner side of the expansion body 240 from an extension end of the shaft arrangement portion 253 to the first through-hole 246 passing a vicinity of an outward curved portion 248 of a distal side expansion portion 247, and an outer arrangement portion 255 extending along the expansion body 240 from the first through-hole 246 to a vicinity of a bottom portion 243 so as to face a receiving space 242a. The inner arrangement portion 254 is separated from the outward curved portion 248 of the distal side expansion portion 247 when the expansion body 240 is expanded. In addition, the outer arrangement portion 255 on which an electrode portion 252 is disposed is bonded and fixed to the expansion body 240 by a bonding portion 256. The bonding portion 256 does not to reach a proximal side curved portion 243a and a distal side curved portion 243b, and a region of the outer arrangement portion 255 on a bottom portion 243 side is in a floating state with respect to the proximal side curved portion 243a and the distal side curved portion 243b. In this manner, the electrode assembly 250 may include a portion along the shaft portion 20. In this case, the fixation of the electrode assembly 250 is not limited to bonding, and the electrode assembly 250 may be fixed by the plurality of electrode engaging portions described above.

Figure 19:
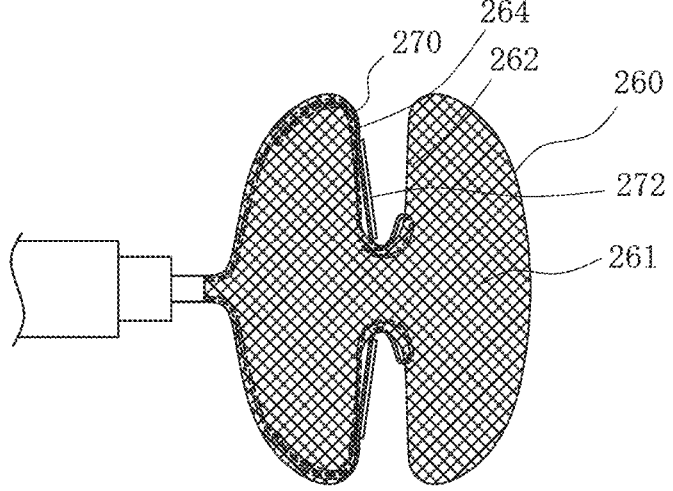
FIG. 19 is an enlarged view of a vicinity of an expansion body according to a seventh modification.
Figure 20:
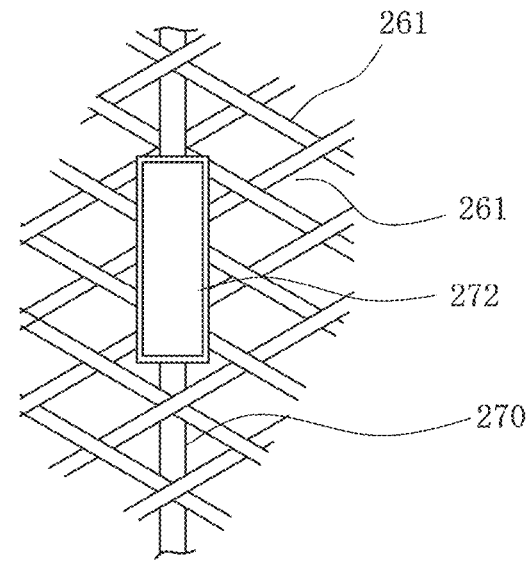
FIG. 20 is an enlarged view of a vicinity of a fixed portion of an electrode portion.

Next, an expansion body 260 and an electrode assembly 270 according to a seventh modification will be described. As illustrated in FIG. 19, the expansion body 260 is formed of a mesh obtained by braiding many wires 261. The expansion body 260 includes a recessed portion 262, and an electrode portion 272 is disposed on a proximal side upright portion 264. As illustrated in FIG. 20, the electrode assembly 270 is engaged with the expansion body 260 by being inserted into a space between the wires 261.

Figure 21:
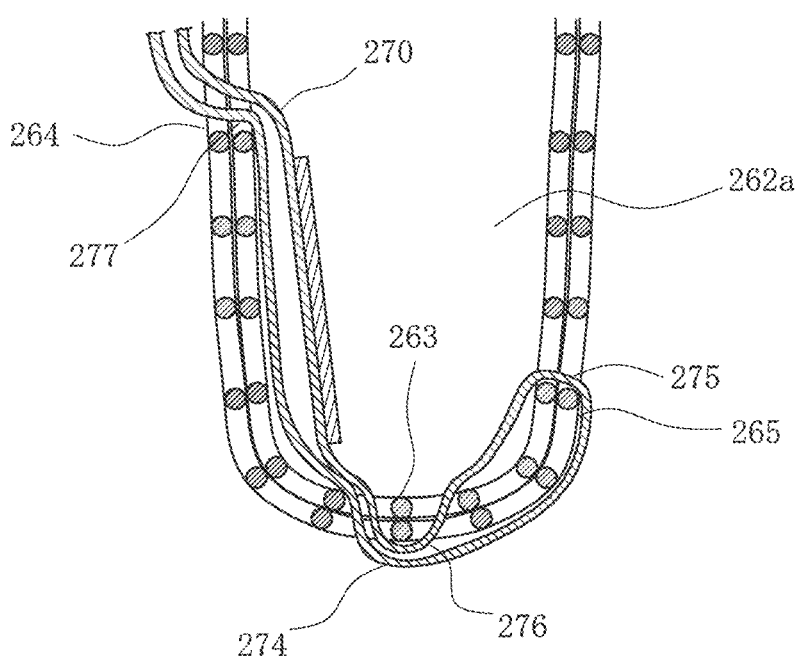
FIG. 21 is a cross-sectional view of the vicinity of the fixed portion of the electrode portion.

As illustrated in FIG. 21, in this modification, the electrode assembly 270 includes a first hook portion 274 engaged with a bottom portion 263, a second hook portion 275 engaged with a distal side upright portion 265, a third hook portion 276 that passes through a radially inner side of the first hook portion 274 to engage with the bottom portion 263, and a fourth hook portion 277 engaged with the proximal side upright portion 264. In addition, an outer arrangement portion 273 on which the electrode portion 272 is disposed faces a receiving space 262a, and is in a floating state with respect to the bottom portion 263.

In this manner, the electrode assembly 270 can be fixed along an outer shape of the expansion body 260 formed of a mesh. The fixation of the electrode assembly 270 is not limited to this modification, and any one of the fixation based on the plurality of electrode engaging portions described above may be applied.

The expansion body may be different from the expansion body 21 in which the plurality of wire portions 50 are fixed to the proximal end fixing portion 31 and the distal end fixing portion 33 of the shaft portion 20, and the expansion body 260 formed of a mesh as described above. For example, an expansion body including a plurality of wire portions may include a proximal side expansion portion and a distal side expansion portion, the proximal side expansion portion may be fixed to a proximal end fixing portion of a shaft portion, and the distal side expansion portion may not be bundled and fixed. In addition, the expansion body including a plurality of wire portions may include a proximal side expansion portion fixed to a proximal end fixing portion, and may not include a distal side expansion portion.

The electrode assembly may include a wide portion that is wider than an electrode engaging portion of the expansion body at an end or an intermediate position in the extending direction serving as an engaged portion. For example, in an example of FIG. 6, the fourth hook portion 76 may be provided with a wide portion to serve as an end of the electrode assembly 22. In addition, wide portions may be provided at portions of the second hook portion 73 forward and rearward of a portion passing through the fourth through-hole 84 so as to be engaged with the second engaging portion 84a.

The plurality of electrode assemblies 22 may have different fixing structures. For example, a structure of the electrode assembly 22 illustrated in FIG. 6 can be employed for two of four wire portions 50, and a structure of the electrode assembly 180 illustrated in FIG. 15 can be employed for the remaining two wire portions 50. In addition, the electrode assemblies 22 may employ other combinations other than the above.

As described above, the medical device 10 according to the present embodiment includes the expansion body 21 configured to expand and contract in a radial direction, the elongated shaft portion 20 including the distal portion 30 that includes the proximal end fixing portion 31 to which a proximal end of the expansion body 21 is fixed, and the plurality of electrode assemblies 22 extending from the proximal end fixing portion 31 of the shaft portion 20 along at least a part of the expansion body 21. The expansion body 21 includes the recessed portion 51 that is recessed radially inward and that defines the receiving space 51a capable of receiving a biological tissue when the expansion body 21 is expanded. The recessed portion 51 includes the radially innermost bottom portion 52 including the proximal side curved portion 52a and the distal side curved portion 52b, the proximal side upright portion 53 extending radially outward from the proximal side curved portion 52a, and the distal side upright portion 54 extending radially outward from the distal side curved portion 52b. Each of the plurality of electrode assemblies 22 includes the electrode portion 61 disposed along the expansion body 21 from the proximal side upright portion 53 or the distal side upright portion 54 to the bottom portion 52 so as to face the receiving space 51a. The proximal side curved portion 52a and the distal side curved portion 52b deform in response to expansion and contraction of the expansion body 21. The electrode portion 61 is in a floating state with respect to the distal side curved portion 52b and the proximal side curved portion 52a. In the medical device 10 configured as described above, since the electrode portion 61 is provided on the electrode assembly 22 separate from the expansion body 21, the electrode portion 61 can be disposed in a position close to the radially innermost bottom portion 52 of the recessed portion 51. In addition, since the electrode portion 61 is not fixed to the proximal side curved portion 52a and the distal side curved portion 52b that are deformed by the expansion and contraction of the expansion body 21 and is in a floating state, the electrode portion 61 disposed at a position close to the bottom portion 52 can be prevented from being damaged due to the deformation of the expansion body 21.

The expansion body 21 may include a plurality of electrode engaging portions configured to engage each of the plurality of electrode assemblies 22 with the expansion body 21. Each of the plurality of electrode assemblies 22 may include an engaged portion that is engaged with a corresponding one of the electrode engaging portions. Each of the electrode engaging portions may be provided in at least one of the bottom portion 52, the proximal side upright portion 52a, and the distal side upright portion 52b. Accordingly, since the electrode assemblies are engaged and fixed to the plurality of electrode engaging portions of the expansion body 21, the electrode portion 61 can be fixed to the expansion body 21 so as not to be displaced.

The expansion body 21 may include the proximal side expansion portion 55 extending radially outward from the proximal end fixing portion 31 of the shaft portion 20 toward a distal direction. The proximal side expansion portion 55 may include the outward curved portion 57 whose distal end is connected to an outer end of the proximal side upright portion 53 and which is curved in a convex shape outward in the radial direction. The proximal side upright portion 53 may include the first through-hole 80 penetrating the expansion body 21. At least one of the plurality of electrode assemblies 22 may include the inner arrangement portion 70 extending along an inner side of the expansion body 21 from the distal portion 30 of the shaft portion 20 to the first through-hole 80 through a vicinity of the outward curved portion 57 of the proximal side expansion portion 55, and the outer arrangement portion 71 extending along the expansion body 21 from the first through-hole 80 to at least the bottom portion 52 so as to face the receiving space 51a. The outward curved portion 57 of the proximal side expansion portion 55 may deform in response to the expansion and contraction of the expansion body 21. The inner arrangement portion 70 may be separated from the outward curved portion 57 of the proximal side expansion portion 55 at least when the expansion body 21 is expanded. The outer arrangement portion 71 may be in a floating state with respect to the distal side curved portion 52b and the proximal side curved portion 52a. Accordingly, the electrode assembly 22 can be prevented from interfering with the expansion body 21 and being damaged.

The expansion body 21 may include the second through-hole 81 in the proximal side curved portion 52a and the third through-hole 82 in the distal side curved portion 52b. The plurality of electrode engaging portions may include the first engaging portion 83 between the second through-hole 81 and the third through-hole 82 of the bottom portion 52. The at least one of the plurality of electrode assemblies 22 may include the first hook portion 72 that functions as the engaged portion, the first hook portion 72 being engaged with the first engaging portion 83 by extending from an extension end of the outer arrangement portion 71, passing through the second through-hole 81, passing through the third through-hole 82 from a radially inner side of the first engaging portion 83, and extending to an outer side of the expansion body 21. Accordingly, the electrode portion 61 is disposed close to the bottom portion 52 of the expansion body 21, the electrode assembly 22 can follow the expansion and contraction of the expansion body 21, and the electrode assembly 22 and the expansion body 21 can be prevented from rubbing against each other and being damaged.

The expansion body 21 may include the fourth through-hole 84 in the distal side upright portion 54. The plurality of electrode engaging portions may include the second engaging portion 84a formed from an edge portion of the fourth through-hole 84. The at least one of the plurality of electrode assemblies 22 may include the second hook portion 73 that functions as the engaged portion, the second hook portion 73 being engaged with the second engaging portion 84a by extending from an extension end of the first hook portion 72 and passing through the fourth through-hole 84 from the outer side to the inner side of the expansion body 21. Accordingly, the electrode assembly 22 can be more strongly fixed to the expansion body 21, and displacement of the electrode portion 61 can be prevented.

The second hook portion 73 may include the folded-back portion 73a passing through the fourth through-hole 84 and extending toward the bottom portion 52 inside the expansion body 21. Accordingly, the electrode assembly 22 can be more reliably fixed to the expansion body 21.

The at least one of the plurality of electrode assemblies 22 may include the third hook portion 74 that functions as the engaged portion, the third hook portion 74 being engaged with the first engaging portion 83 by extending from an extension end of the second hook portion 73, passing through the second through-hole 81 from the inner side of the expansion body 21, and extending to the outer side of the expansion body 21. Accordingly, since the electrode assembly 22 can be fixed to the expansion body 21 at a portion further extending to the distal side of the electrode portion 61, the displacement of the electrode portion 61 can be more effectively prevented.

The at least one of the plurality of electrode assemblies 22 may include the first extension portion 75 extending from an extension end of the third hook portion 74 and extending between the outer arrangement portion 71 and the proximal side upright portion 53 toward the first through-hole 80. The medical device 10 may further include the first cover 65 configured to cover the proximal side upright portion 53 and the first extension portion 75. Accordingly, when the expansion body 21 is expanded or contracted, the electrode assembly 22 can reliably follow movement of the proximal side upright portion 53, and the electrode assembly 22 can be prevented from contacting an unintended location and being damaged.

The at least one of the plurality of electrode assemblies 22 may include the electrode portion 61 on the outer arrangement portion 71. The first cover 65 may be sandwiched between the outer arrangement portion 71 and the first extension portion 75. Accordingly, the electrode assembly 22 can follow the expansion and contraction of the expansion body 21 while exposing the electrode portion 61 to an outside of the first cover 65.

The plurality of electrode engaging portions may include the third engaging portion 80a formed from an edge portion of the first through-hole 80. The at least one of the plurality of electrode assemblies 22 may include the first extension portion 75 extending from an extension end of the third hook portion 74 and extending between the outer arrangement portion 71 and the proximal side upright portion 53 toward the first through-hole 80, and the fourth hook portion 76 that functions as the engaged portion, the fourth hook portion 76 being engaged with the third engaging portion 80a by extending from an extension end of the first extension portion 75 and passing through the first through-hole 80. Accordingly, the electrode assembly 22 can be more reliably fixed to the expansion body 21, and the displacement of the electrode portion 61 can be prevented.

The fourth hook portion 76 may include the crank-shaped portion 76a extending from the extension end of the first extension portion 75, passing through the first through-hole 80 and extending along the inner side of the expansion body 21. Accordingly, the electrode assembly 22 can be more reliably engaged with the expansion body 21.

The at least one of the plurality of electrode assemblies 22 may include the second extension portion 77 extending from an extension end of the crank-shaped portion 76a and extending along the inner arrangement portion 70 on a radially inner side of the inner arrangement portion 70. The medical device 10 may further include the second cover 66 configured to cover the second extension portion 77, the inner arrangement portion 70, and the proximal side expansion portion 55. Accordingly, since the electrode assembly 22 can be moved to follow the proximal side expansion portion 55 when the expansion body 21 is expanded or contracted, the electrode assembly 22 can be prevented from contacting an unintended location and being damaged.

The expansion body 130 may include the second through-hole 151 in the bottom portion 133. The plurality of electrode engaging portions may include the first engaging portion 151a formed from an edge portion of the second through-hole 151. At least one of the plurality of electrode assemblies 140 may include the first hook portion 145 that functions as the engaged portion, the first hook portion 145 extending from an extension end of the outer arrangement portion 144, passing through the second through-hole 151, and extending to a radially inner side of the bottom portion 133. The first hook portion 145 may include the wide portion 145a that is wider than a portion of the first hook portion 145 passing through the second through-hole 151 and is engaged with the first engaging portion 151a. Accordingly, the electrode portion 142 is disposed close to the bottom portion 133 of the expansion body 130, the electrode assembly 140 can follow expansion and contraction of the expansion body 130, and the electrode assembly 140 and the expansion body 130 can be prevented from rubbing against each other and being damaged.

The plurality of electrode engaging portions may include the second engaging portion 156a formed from an edge portion of the third through-hole 156. The first hook portion 145 may include the wide portion 145a that is wider than a portion of the first hook portion 145 passing through the third through-hole 156 and is engaged with the second engaging portion 156a. Accordingly, since the electrode assembly 140 is engaged with the second engaging portion 156a by the wide portion 145a while being engaged with the first engaging portion 157, the electrode assembly 140 can be more reliably fixed to the expansion body 130.

The expansion body 130 may include the second through-hole 155 in the proximal side curved portion 133a and the fourth through-hole 158 in the distal side upright portion 132. The plurality of electrode engaging portions may include the first engaging portion 157 formed from an edge portion of the second through-hole 155 and the second engaging portion 158a formed from an edge portion of the fourth through-hole 158. The at least one of the plurality of electrode assemblies 140 may include the first hook portion 145 that functions as the engaged portion, the first hook portion 145 being engaged with the first engaging portion 157 by extending from an extension end of the outer arrangement portion 144, passing through the second through-hole 155, passing through the fourth through-hole 158 from a radially inner side of the first engaging portion 157, and extending to an outer side of the expansion body 130. The first hook portion 145 may include the wide portion 145a that is wider than a portion of the first hook portion 145 passing through the fourth through-hole 158 and is engaged with the second engaging portion 158a. Accordingly, since the electrode assembly 140 can further extend to a distal side of the electrode portion 142 and fixed to the expansion body 130, displacement of the electrode portion 142 can be more effectively prevented.

The expansion body 100 may include the second through-hole 121 in the distal side curved portion 103b and the third through-hole 122 in the proximal side curved portion 103a. The plurality of electrode engaging portions may include the first engaging portion 123 formed between the second through-hole 121 and the third through-hole 122 and the fourth engaging portion 120a formed from an edge portion of the first through-hole 120. At least one of the plurality of electrode assemblies 110 may include the first hook portion 115 that functions as the engaged portion, the first hook portion 115 being engaged with the first engaging portion 123 by extending from an extension end of the outer arrangement portion 114, passing through the second through-hole 121, passing through the third through-hole 122 from a radially inner side of the first engaging portion 123, and extending to an outer side of the expansion body 100, the first extension portion 116 extending from an extension end of the first hook portion 115 and extending between the outer arrangement portion 114 and the proximal side upright portion 104 toward the first through-hole 120, and the fourth hook portion 117 that functions as the engaged portion, the fourth hook portion 117 being engaged with the fourth engaging portion 120a by extending from an extension end of the first extension portion 116 and passing through the first through-hole 120. Accordingly, the electrode assembly 110 can be engaged and fixed at two locations, that is, the first engaging portion 123 and the fourth engaging portion 102a, and the electrode portion can be fixed with a simple structure.

At least one of the plurality of electrode assemblies 210 may be bonded and fixed to the expansion body 200 at the proximal side upright portion 204 or the distal side upright portion. Accordingly, the electrode portion 212 can be fixed to the expansion body 200 while making a portion of the electrode portion 212 on the bottom portion 203 side in a floating state with respect to the expansion body 200.

The expansion body 220 may include the first through-hole 226 in the distal side upright portion 225. At least one of the plurality of electrode assemblies 230 may include the inner arrangement portion 233 extending along an inner side of the expansion body 220 from the distal portion 30 of the shaft portion 20 to the first through-hole 226 of the distal side upright portion 225 beyond the proximal side upright portion 224, and an outer arrangement portion 234 folded back with respect to the inner arrangement portion 233 and extending along the expansion body 220 from the first through-hole 226 to the bottom portion 223 so as to face the receiving space 222a. Accordingly, the electrode portion 232 can be disposed on a distal side upright portion 225 side with a simple structure.

The shaft portion 20 may include the shaft extension portion 32 extending inside the expansion body 240 along a central axis of the expansion body 240 from the proximal end fixing portion 31 and the distal end fixing portion 33 to which a distal end of the expansion body 240 is fixed. The expansion body 240 may include the distal side expansion portion 247 extending radially outward from the distal end fixing portion 33 of the shaft portion 20 toward a proximal direction. The distal side expansion portion 247 may include the outward curved portion 248 whose proximal end is connected to an outer end of the distal side upright portion 245 and which is curved in a convex shape outward in the radial direction. The distal side upright portion 245 may include the first through-hole 246. At least one of the plurality of electrode assemblies 250 may include the shaft arrangement portion 253 extending along the shaft extension portion 32 from the proximal end fixing portion 31 of the shaft portion 20 to the distal end fixing portion 33, the inner arrangement portion 254 extending along the inner side of the expansion body 240 from an extension end of the shaft arrangement portion 253 to the first through-hole 246 through a vicinity of the outward curved portion 248 of the distal side expansion portion 247, and the outer arrangement portion 255 extending along the expansion body 240 from the first through-hole 246 to at least the bottom portion 243 so as to face the receiving space 242a. The outward curved portion 248 of the distal side expansion portion 247 may deform in response to expansion and contraction of the expansion body 240. The inner arrangement portion 254 may be separated from the outward curved portion 248 of the distal side expansion portion 247 at least when the expansion body 240 is expanded. The outer arrangement portion 255 may be in a floating state with respect to the distal side curved portion 243b and the proximal side curved portion 243a. Accordingly, the electrode assembly 250 can be disposed while using the shaft portion 20, and the electrode assembly 250 can be made less likely to interfere with the expansion and contraction of the expansion body 240.

The expansion body 170 may include the second through-hole 191 in the proximal side curved portion 173a, the third through-hole 192 in the distal side curved portion 173b, and the fourth through-hole 194 in the distal side upright portion 175. The plurality of electrode engaging portions may include the first engaging portion 193 formed between the second through-hole 191 and the third through-hole 192 of the bottom portion 173 and the second engaging portion 194a formed at an edge portion of the fourth through-hole 194. At least one of the plurality of electrode assemblies 180 may include the first hook portion 185 that functions as the engaged portion, the first hook portion 185 being engaged with the first engaging portion 193 by extending from an extension end of the outer arrangement portion 184, passing through the second through-hole 191, passing through the third through-hole 192 from a radially inner side of the first engaging portion 193, and extending to an outer side of the expansion body 170, and the second hook portion 187 that functions as the engaged portion, the second hook portion 187 being engaged with the second engaging portion 194a by extending from an extension end of the first hook portion 185 and passing through the fourth through-hole 194 from the outer side to an inner side of the expansion body 170. The electrode portion 182 may be disposed between the first hook portion 185 and the second hook portion 187. Accordingly, when the electrode portion 182 is disposed on a distal side upright portion 175 side, the electrode assembly 180 can be firmly engaged and fixed to the expansion body 170, and displacement of the electrode portion 182 can be prevented.

The expansion body 260 may be formed of a mesh obtained by braiding many wires 261. At least one of the plurality of electrode assemblies 270 may be inserted between the wires 261 and engaged and fixed. Accordingly, the electrode assembly 270 can also be fixed to the expansion body 260 formed of a mesh, and the electrode portion 272 can be disposed in a vicinity of the bottom portion 263 of the recessed portion 262.

The detailed description above describes embodiments of an energy-applying medical device representing examples of the new energy-applying medical device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

REFERENCE SIGNS LIST 10 medical device
11 guide wire
20 shaft portion
21 expansion body
22 electrode assembly
23 operation unit
25 housing sheath
26 pulling shaft
30 distal portion
31 proximal end fixing portion 32 shaft extension portion
33 distal end fixing portion
35 distal member
40 housing
41 operation dial
42 conversion mechanism
50 wire portion
51 recessed portion
51a receiving space
52 bottom portion
52a proximal side curved portion
52b distal side curved portion
53 proximal side upright portion
54 distal side upright portion
55 proximal side expansion portion
57 outward curved portion
58 outer edge portion
59 back support portion
60 wiring portion
60a electric wire portion
60b adhesive layer
60c insulating layer
61 electrode portion
62 connection portion
65 first cover
66 second cover
70 inner arrangement portion
71 outer arrangement portion
72 first hook portion
73 second hook portion
73a folded-back portion
74 third hook portion
75 first extension portion
76 fourth hook portion
76a crank-shaped portion
77 second extension portion
80 first through-hole
80a third engaging portion
81 second through-hole
82 third through-hole
83 first engaging portion
84 fourth through-hole
84a second engaging portion

What is claimed is:

1. A medical device comprising:

an expansion body configured to expand and contract in a radial direction;

an elongated shaft including a distal portion that includes a proximal end fixing portion to which a proximal end of the expansion body is fixed;

a plurality of electrode assemblies extending from the proximal end fixing portion of the shaft along at least a part of the expansion body;

the expansion body includes a recessed portion that is recessed radially inward relative to portions of the expansion body proximal and distal of the recessed portion and that defines a receiving space to receive biological tissue when the expansion body is expanded while positioned in a hole in the biological tissue;

the recessed portion of the expansion body including a radially innermost bottom portion including a proximal side curved portion and a distal side curved portion, a proximal side upright portion extending radially outward from the proximal side curved portion, and a distal side upright portion extending radially outward from the distal side curved portion, the proximal side curved portion being proximal of the distal side curved portion;

each of the plurality of electrode assemblies including an electrode portion disposed along the expansion body from the proximal side upright portion to the bottom portion or from the distal side upright portion to the bottom portion, the electrode portion facing the receiving space;

the proximal side curved portion and the distal side curved portion being deformable in response to expansion and contraction of the expansion body;

the electrode portion is being in a floating state with respect to the distal side curved portion and the proximal side curved portion;

the expansion body including a plurality of electrode engaging portions that each engage a respective one of the plurality of electrode assemblies;

each of the plurality of electrode assemblies including an engaged portion that is engaged with a corresponding one of the electrode engaging portions;

each of the electrode engaging portions is provided in at least one of the bottom portion, the proximal side upright portion, and the distal side upright portion of the recessed portion of the expansion body;

the expansion body including a proximal side expansion portion extending radially outward from the proximal end fixing portion of the shaft toward a distal direction, and the proximal side expansion portion including an outward curved portion whose distal end is connected to a radially outer end of the proximal side upright portion, the outward curved portion being curved in a convex shape outward in the radial direction;

the proximal side upright portion including a first through-hole passing through the expansion body;

at least one of the plurality of electrode assemblies including an inner arrangement portion and an outer arrangement portion, the inner arrangement portion extending inside of the proximal side expansion portion from the distal portion of the shaft to the first through-hole, the outer arrangement portion extending along the expansion body from the first through-hole to at least the bottom portion of the recessed portion of the expansion body so as to face the receiving space;

the outward curved portion of the proximal side expansion portion is configured to deform in response to the expansion and contraction of the expansion body, the inner arrangement portion is separated from the outward curved portion of the proximal side expansion portion at least when the expansion body is expanded; and the outer arrangement portion is in a floating state with respect to the distal side curved portion and the proximal side curved portion.

2. The medical device according to claim 1, wherein the inner arrangement portion extends along an inner side of the expansion body from the distal portion of the shaft to the first through-hole while also extending along the outward curved portion of the proximal side expansion portion.

3. The medical device according to claim 1, wherein the expansion body includes a second through-hole in the proximal side curved portion and a third through-hole in the distal side curved portion, the plurality of electrode engaging portions include a first engaging portion between the second through-hole and the third through-hole of the bottom portion, and the at least one of the plurality of electrode assemblies includes a first hook portion that is the engaged portion, the first hook portion being engaged with the first engaging portion by extending from an extension end of the outer arrangement portion, passing through the second through-hole, passing through the third through-hole from a radially inner side of the first engaging portion, and extending to an outer side of the expansion body.

4. The medical device according to claim 3, wherein the expansion body includes a fourth through-hole in the distal side upright portion, the plurality of electrode engaging portions include a second engaging portion constituted by an edge portion of the fourth through-hole, and the at least one of the plurality of electrode assemblies includes a second hook portion that is the engaged portion, the second hook portion being engaged with the second engaging portion by extending from an extension end of the first hook portion and passing through the fourth through-hole from the outer side to the inner side of the expansion body.

5. The medical device according to claim 4, wherein the second hook portion includes a folded-back portion passing through the fourth through-hole and extending inside the expansion body toward the bottom portion.

6. The medical device according to claim 4, wherein the at least one of the plurality of electrode assemblies includes a third hook portion that functions as the engaged portion, the third hook portion being engaged with the first engaging portion by extending from an extension end of the second hook portion, passing through the second through-hole from the inner side of the expansion body, and extending to the outer side of the expansion body.

7. The medical device according to claim 6, wherein the at least one of the plurality of electrode assemblies includes a first extension portion extending from an extension end of the third hook portion and extending between the outer arrangement portion and the proximal side upright portion toward the first through-hole, and the medical device further comprises a first cover that covers the proximal side upright portion and the first extension portion.

8. The medical device according to claim 7, wherein the at least one of the plurality of electrode assemblies includes the electrode portion on the outer arrangement portion, and the first cover is sandwiched between the outer arrangement portion and the first extension portion.

9. The medical device according to claim 6, wherein the plurality of electrode engaging portions include a third engaging portion constituted by an edge portion of the first through-hole, and the at least one of the plurality of electrode assemblies includes a first extension portion extending from an extension end of the third hook portion and extending between the outer arrangement portion and the proximal side upright portion toward the first through-hole, and a fourth hook portion that is the engaged portion, the fourth hook portion being engaged with the third engaging portion by extending from an extension end of the first extension portion and passing through the first through-hole.

10. The medical device according to claim 9, wherein the fourth hook portion includes a crank-shaped portion extending from the extension end of the first extension portion, passing through the first through-hole, and extending along the inner side of the expansion body.

11. The medical device according to claim 10, wherein the at least one of the plurality of electrode assemblies includes a second extension portion extending from an extension end of the crank-shaped portion and extending along the inner arrangement portion on a radially inner side of the inner arrangement portion, and the medical device further comprises a second cover covering the second extension portion, the inner arrangement portion, and the proximal side expansion portion.

12. The medical device according to claim 3, wherein the plurality of electrode engaging portions include a second engaging portion constituted by an edge portion of the third through-hole, and the first hook portion includes a wide portion that is wider than a portion of the first hook portion passing through the third through-hole and is engaged with the second engaging portion.

13. The medical device according to claim 1, wherein the expansion body includes a second through-hole in the bottom portion, the plurality of electrode engaging portions include a first engaging portion constituted by an edge portion of the second through-hole, the at least one of the plurality of electrode assemblies includes a first hook portion that is the engaged portion, the first hook portion extending from an extension end of the outer arrangement portion, passing through the second through-hole, and extending to a radially inner side of the bottom portion, and the first hook portion includes a wide portion that is wider than a portion of the first hook portion passing through the second through-hole and is engaged with the first engaging portion.

14. The medical device according to claim 1, wherein the expansion body includes a second through-hole in the proximal side curved portion and a fourth through-hole in the distal side upright portion, the plurality of electrode engaging portions include a first engaging portion constituted by an edge portion of the second through-hole and a second engaging portion constituted by an edge portion of the fourth through-hole, the at least one of the plurality of electrode assemblies includes a first hook portion that is the engaged portion, the first hook portion being engaged with the first engaging portion by extending from an extension end of the outer arrangement portion, passing through the second through-hole, passing through the fourth through-hole from a radially inner side of the first engaging portion, and extending to an outer side of the expansion body, and the first hook portion includes a wide portion that is wider than a portion of the first hook portion passing through the fourth through-hole and is engaged with the second engaging portion.

15. The medical device according to claim 1, wherein the expansion body includes a second through-hole in the distal side curved portion and a third through-hole in the proximal side curved portion, the plurality of electrode engaging portions include a first engaging portion formed between the second through-hole and the third through-hole, and a fourth engaging portion formed from an edge portion of the first through-hole, and the at least one of the plurality of electrode assemblies includes a first hook portion that is the engaged portion, the first hook portion being engaged with the first engaging portion by extending from an extension end of the outer arrangement portion, passing through the second through-hole, passing through the third through-hole from a radially inner side of the first engaging portion, and extending to an outer side of the expansion body, a first extension portion extending from an extension end of the first hook portion and extending between the outer arrangement portion and the proximal side upright portion toward the first through-hole, and a fourth hook portion that is the engaged portion, the fourth hook portion being engaged with the fourth engaging portion by extending from an extension end of the first extension portion and passing through the first through-hole.

16. The medical device according to claim 1, wherein at least one electrode assembly of the plurality of electrode assemblies is bonded and fixed to the expansion body at the proximal side upright portion or the distal side upright portion.

17. The medical device according to claim 16, wherein the shaft includes a shaft extension portion extending inside the expansion body along a central axis of the expansion body from the proximal end fixing portion, the shaft also including a distal end fixing portion to which a distal end of the expansion body is fixed, the expansion body includes a distal side expansion portion extending radially outward from the distal end fixing portion of the shaft toward a proximal direction, the distal side expansion portion includes an outward curved portion whose proximal end is connected to an outer end of the distal side upright portion and which is curved in a convex shape outward in the radial direction, the distal side upright portion includes a first through-hole, at least one of the plurality of electrode assemblies includes a shaft arrangement portion extending along the shaft extension portion from the proximal end fixing portion of the shaft to the distal end fixing portion, an inner arrangement portion extending along the inner side of the expansion body from an extension end of the shaft arrangement portion to the first through-hole through a vicinity of the outward curved portion of the distal side expansion portion, and an outer arrangement portion extending along the expansion body from the first through-hole to at least the bottom portion so as to face the receiving space, the outward curved portion of the distal side expansion portion is deformable so that the outward curved portion of the distal side expansion portion deforms in response to the expansion and contraction of the expansion body, the inner arrangement portion is separated from the outward curved portion of the distal side expansion portion at least when the expansion body is expanded, and the outer arrangement portion is in a floating state with respect to the distal side curved portion and the proximal side curved portion.

18. The medical device according to claim 1, wherein the expansion body includes a first through-hole in the distal side upright portion, and at least one of the plurality of electrode assemblies includes an inner arrangement portion extending along the inner side of the expansion body from the distal portion of the shaft to the first through-hole of the distal side upright portion beyond the proximal side upright portion, and an outer arrangement portion folded back with respect to the inner arrangement portion and extending along the expansion body from the first through-hole to the bottom portion so as to face the receiving space.

19. The medical device according to claim 1, wherein the expansion body includes a second through-hole in the proximal side curved portion, a third through-hole in the distal side curved portion, and a fourth through-hole in the distal side upright portion, the plurality of electrode engaging portions include a first engaging portion formed between the second through-hole and the third through-hole of the bottom portion, and a second engaging portion formed at an edge portion of the fourth through-hole, the at least one of the plurality of electrode assemblies includes a first hook portion that is the engaged portion, the first hook portion being engaged with the first engaging portion by extending from an extension end of the outer arrangement portion, passing through the second through-hole, passing through the third through-hole from a radially inner side of the first engaging portion, and extending to an outer side of the expansion body, and a second hook portion that is the engaged portion, the second hook portion being engaged with the second engaging portion by extending from an extension end of the first hook portion and passing through the fourth through-hole from the outer side to the inner side of the expansion body, and the electrode portion is disposed between the first hook portion and the second hook portion.

20. The medical device according to claim 1, wherein the expansion body is comprised of a mesh obtained by braiding a plurality of wires, and at least one electrode assembly of the plurality of electrode assemblies is positioned between plural wires of the plurality of the wires and is engaged and fixed relative to the plural wires.

21. A medical device comprising:

an expansion body configured to expand and contract in a radial direction;

an elongated shaft including a distal portion that includes a proximal end fixing portion to which a proximal end of the expansion body is fixed;

a plurality of electrode assemblies that each include an elongated wiring portion having a lengthwise extent and an electrode portion positioned at an intermediate portion of the elongated wiring portion so that the electrode portion overlies a part of the elongated wiring portion;

the expansion body includes a recessed portion that is recessed radially inward relative to portions of the expansion body proximal and distal of the recessed portion and that defines a receiving space to receive biological tissue when the expansion body is expanded while positioned in a hole in the biological tissue;

the recessed portion of the expansion body including a radially innermost bottom portion including a proximal side curved portion and a distal side curved portion, a proximal side upright portion extending radially outward from the proximal side curved portion, and a distal side upright portion extending radially outward from the distal side curved portion, the proximal side curved portion being proximal of the distal side curved portion;

the electrode portion of each of the plurality of electrode assemblies facing the receiving space and being disposed along the expansion body from the proximal side upright portion toward the bottom portion or from the distal side upright portion toward the bottom portion;

the proximal side curved portion and the distal side curved portion being deformable in response to expansion and contraction of the expansion body; and the electrode portion and the part of the elongated wiring portion that the electrode portion overlies of each electrode assembly being movable relative to the distal side curved portion and the proximal side curved portion to prevent damage to the electrode portion when the proximal side curved portion and the distal side curved portion deform in response to expansion and contraction of the expansion body.

22. The medical device according to claim 21, wherein the elongated wiring portion of each electrode assembly passes through a first through hole in the expansion portion and passes through a second through hole in the expansion body that is spaced from the first through hole, the second through hole being located closer to the radially innermost bottom portion than the first through hole.

\* \* \* \* \*